(12) United States Patent
Comins et al.

(10) Patent No.: US 8,389,732 B2
(45) Date of Patent: Mar. 5, 2013

(54) SYNTHESIS AND REGIOSELECTIVE SUBSTITUTION OF 6-HALO- AND 6-ALKOXY NICOTINE DERIVATIVES

(75) Inventors: Daniel L. Comins, Raleigh, NC (US);
Florence F. Wagner, Duluth, GA (US);
Pauline Ondachi, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 155 days.

(21) Appl. No.: 12/879,109

(22) Filed: Sep. 10, 2010

(65) Prior Publication Data

US 2010/0331323 A1 Dec. 30, 2010

Related U.S. Application Data

(62) Division of application No. 11/693,276, filed on Mar. 29, 2007, now Pat. No. 7,820,826.

(60) Provisional application No. 60/787,116, filed on Mar. 29, 2006.

(51) Int. Cl.
*C07D 401/00* (2006.01)
*A61K 31/44* (2006.01)

(52) U.S. Cl. ..................... 546/276.4; 514/343

(58) Field of Classification Search ............... 546/26
See application file for complete search history.

(56) References Cited

U.S. PATENT DOCUMENTS

| | | | |
|---|---|---|---|
| 2,315,312 A | 3/1943 | Burger |
| 4,321,387 A | 3/1982 | Chavdarian et al. |
| 5,594,011 A | 1/1997 | McDonald et al. |
| 5,677,459 A | 10/1997 | McDonald et al. |
| 5,723,477 A | 3/1998 | McDonald et al. |
| 6,995,265 B2 | 2/2006 | Comins et al. |
| 7,067,672 B2 | 6/2006 | Comins et al. |
| 7,112,678 B2 | 9/2006 | King et al. |
| 7,132,545 B2 | 11/2006 | Comins et al. |
| 7,179,917 B2 | 2/2007 | Comins et al. |
| 7,304,160 B2 | 12/2007 | King et al. |
| 2007/0112195 A1 | 5/2007 | Comins et al. |

OTHER PUBLICATIONS

Seeman et al Analytical Chemistry 1988, 60, 2120-2127.*
Terent'eve et al Zhurnal Obshchei Khimii 1957, 27, 3170-3173—abstract.*
Shirshova et al Khimiya Geterotsiklischeskikh Soedinenii 1974, 8, 1133-1136—abstract.*
Shirshova et al Izvestiya Akademii Nauk Moldayskoi SSR, Biologicheskie i Khimicheskie Nauki 1973, 2, 76-8—abstract.*
Shirshova et al Khimiya Geterotsiklicheskikh Soedinenii 1973, 7, 952-3—abstract.*
Mahboobi S et al. Synthesis of enantiomerically pure (-)-(S)-brevicolline. J. Nat. Prod. 1999; 62: 577-579.
Database Reaxys [Online]. 1976, Lazurjevski, XRN 30713.
Müller W et al. Ein einfacher zugang zu 1,4-disubstituirten beta-carbolinderivaten. Angew Chemie. 1975; 87: 385-386.
Mahboobi S et al. Removal of the pyrrolidine substituent by dehydrogenation of 4-pyrrolidin-2-yl-e,r-dihydro- and 1,2,3,4-tetrahydroisoquinolines. Arch. Pharm. 1994; 327: 417-428.
Database Reaxys [Online]. 1974, Shirshova, XRN 561678.
Database Reaxys [Online]. 1973, Shirshova, XRN 679479.
Database Reaxys [Online]. 1972, Shirshova, XRN 567483.
Database Reaxys [Online]. 1984, Dallacker F et al. Derivatives of 1,3-benzdioxoles.
Supplementary European Search Report, EP 07754151, Apr. 4, 2011.
Chavdarian CG et al. Synthesis of optically active nicotinoids. J. Org. Chem. 1982; 47(6): 1069-1073.
Fessenden and Fessenden. Willard Grant Press, Boston, MA 1982, Organic Chemistry 2nd Ed. pp. 743-761.
Seeman JI et al. Organometallic methylation of nicotine and nicotine N-oxide. Reaction pathways and racemization mechanisms. J. Org. Chem. 1983; 48(25): 4899-4904.
Jacob P III et al. Disposition kinetics of nicotine and cotinine enantiomers in rabbits and beagle dogs. J. Pharm. Sci. 1988; 77(5): 396-400.
Matsuzaki T et al. Germination and growth inhibition of surface lipids from nicotiana species and identification of sucrose esters. Agric. Biol. Chem. 1988; 52(8): 1889-1897.
Damaj MI et al. Pharmacology of novel nicotinic analogs. Drug Development Research. 1996; 38(3-4): 177-187.
Dukat M et al. Synthesis, receptor binding and QSAR studies on 6-substituted nicotine derivatives as cholinergic ligands. Eur. J. Med. Chem. 1999; 34: 31-40.
Dehn DL et al. Nicotine and cotinine adducts of a melanin intermediate demonstrated by matrix-assisted laser desorption/ionization time-of-flight mass spectrometry. Chem. Res. Toxicol. 2001; 14(3): 275-279.
Lee M et al. A comparison of the binding of three series of nicotinic ligands. Bioorganic & Medicinal Chemistry Letters, 2002; 12: 1989-1992.
Ferretti G et al. Binding of nicotine and homoazanicotine analogues at neuronal nicotinic acetylcholinergic (nACh) receptors. Bioorganic & Medicinal Chemistry Letters. 2003; 13: 733-735.
Yilmaz F et al. In vitro microsomal metabolism of N-benzyl and N-benzoylnornicotine derivates by rat. European Journal of Drug Metabolism and Pharmacokinetics. 2004; 29(4): 249-256.
Comins DL et al. Synthesis of C-4 substituted nicotine derivatives via an N-acylpyridinium salt of (S)—nicotine. Organic Letters. 2005; 7(22): 5051-5062.
Dörwald FZ. Side reactions in organic synthesis: a guide to successful synthesis design. 2005. Wiley-VCH GmbH & Co. KGaA, Weinheim, Germany.
Février FC et al. Regioselective C-2 and C-6 substitution of (S)-nicotine and nicotine derivatives. Organic Letters. 2005; 7(24): 5457-5460.
Wagner et al. "Six-Step Synthesis of (S)-Brevicolline from (S)-Nicotine", *Org. Lett.* 8(16):3549-3552.
Wagner et al. "Expedient Five-Step Synthesis of SIB-1508Y from Natural Nicotine", *J. Org. Chem.* 71:8673-8675 (2006).
Notification of Transmittal of the International Search Report for PCT/US07/07585, mailed Oct. 26, 2007.
U.S. Appl. No. 11/924,644, filed Oct. 26, 2007, King et al.

(Continued)

*Primary Examiner* — John Mabry

(74) *Attorney, Agent, or Firm* — Myers Bigel Sibley & Sajovec, P.A.

(57) ABSTRACT

The present invention provides active compounds for modulating nicotinic acetylcholine receptors and methods of making the same. The methods of preparing the active compounds utilize different intermediate compounds.

21 Claims, No Drawings

OTHER PUBLICATIONS

Seeman JI et al. Preparation of hydroxyalkyl-substituted nicotinoids. J. Org. Chem. 1986;51:1548-1551.

Gros P et al. Lithiation of 2-heterosubstituted pyridines with BuLi-LiDMAE: evidence for regiospecificity at C-6. J. Org. Chem. 2002;67:234-237.

Wagner F and Comins DL Recent advances in the synthesis of nicotine and its derivatives. Tetrahedron. 2007;63:8065-8082.

Ondachi PW and Comins DL. Synthesis and regioselective substitution of C-6 alkoxy derivatives of (S)-nicotine. Tetrahedron Letters. 2008;49:569-572.

Lewis RJ Hawley's Condensed Chemical Dictionary, 13th Ed. 1997; 569. John Wiley & Sons, NY.

Muci AR and Buchwald SL. Practical palladium catalysts for C-N and C-O bond formation. Topics in Current Chemistry. 2002; 219(Cross-Coupling Reactions): 131-209.

Evano G et al. Copper-mediated coupling reactions and their applications in natural products and designed biomolecules synthesis. Chemical Reviews. 2008; 108(8): 3054-3131.

Monnier F and Taillefer M. Catalytic C-C, C-N, and C-O Ullmann-type coupling reactions: copper makes a difference. Angewandte Chemie, International Edition. 2008; 47(17): 3096-3099.

\* cited by examiner

SYNTHESIS AND REGIOSELECTIVE SUBSTITUTION OF 6-HALO- AND 6-ALKOXY NICOTINE DERIVATIVES

CROSS-REFERENCE TO RELATED APPLICATION

This patent application is a divisional of and claims priority to U.S. patent application Ser. No. 11/693,276, filed Mar. 29, 2007, now U.S. Pat. No. 7,820,826 now allowed, and claims the benefit of U.S. Provisional Application No. 60/787,116, filed Mar. 29, 2006, the disclosure of each of which is hereby incorporated by reference in its entirety.

FIELD OF THE INVENTION

The present invention concerns methods and intermediates useful for the synthesis of compounds active for modulating nicotinic acetylcholine receptors.

BACKGROUND OF THE INVENTION

Acetylcholine receptors are involved in the modulation of a variety of physiological and behavioral functions, including neuroendocrine function, respiration, mood, motor control and function, focus and attention, concentration, memory and cognition, and substance abuse. Ligands for acetylcholine receptors have been demonstrated to have effects on attention, cognition, appetite, substance abuse, memory, extrapyramidal function, cardiovascular function, pain and gastrointestinal motility and function. The distribution of acetylcholine receptors that bind nicotine, i.e., nicotinic acetylcholine receptors, are found in muscle, autonomic ganglia, the gastrointestinal tract and the cardiovascular system (see, e.g., U.S. Pat. No. 5,594,011).

Acetylcholine receptors have been shown to be decreased, among other things, in the brains of patients suffering from Alzheimer's disease, and Parkinson's disease, as well as diseases associated with dementia, motor dysfunction and cognitive impairment. Such correlation between acetylcholine receptors and nervous system disorders suggest that compounds that modulate acetylcholine receptors will have beneficial therapeutic effects for many human nervous system disorders. U.S. Pat. No. 5,594,011 to McDonald et al., assigned to SIBIA Neuroscience, describes compounds such as SIB-1508Y that modulate nicotinic acetylcholine receptors. Such compounds are useful for, among other things, Parkinson's disease. See also U.S. Pat. No. 5,723,477 to McDonald et al. Unfortunately, nicotine analogs are difficult compounds to synthesize, and there is continuing need for new methods of making the same, as well as intermediates useful for the synthesis of nicotine analogs.

SUMMARY OF THE INVENTION

A first aspect of the present invention is a method for making a compound of Formula Ia:

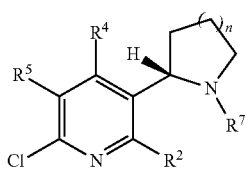

(Ia)

wherein:
n is 0, 1, 2 or 3;
$R^2$ is selected from the group consisting of H, alkyl, aryl, alkoxy and halo, preferably H;
$R^4$ and $R^5$ are independently selected from the group consisting of alkyl, aryl, heteroaryl, alkenyl, alkynyl, alkoxy, aryloxy, halo, amino, $SiR^{20}R^{21}R^{22}$, $SnR^{20}R^{21}R^{22}$ wherein $R^{20}R^{21}$ and $R^{22}$ are each independently alkyl, aryl, halo, hydroxy or alkoxy; and
$R^7$ is H, alkyl, aryl, amino, alkoxy, cyano or acyl; comprising:
(a) metalating a compound of the formula IIa, IIb, IIc or IId:

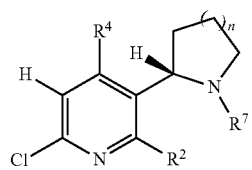

(IIa)

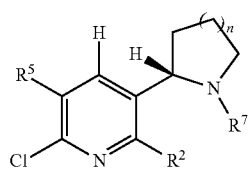

(IIb)

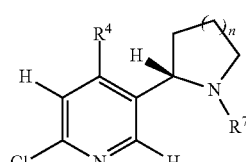

(IIc)

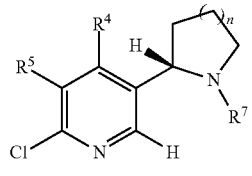

(IId)

with a metal base to form an organometallic intermediate compound; and then
(b) reacting the organometallic intermediate compound with an electrophile to produce a compound of Formula Ia.

A second aspect of the present invention is a method of making a compound of Formula III

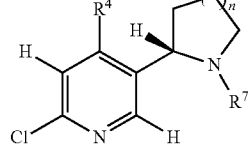

(III)

wherein:
n is 0, 1, 2 or 3;
$R^2$, $R^4$ and $R^5$ are each independently H, alkyl, aryl, heteroaryl, alkenyl, alkynyl, $SiR^{20}R^{21}R^{22}$, $SnR^{20}R^{21}R^{22}$, halo, amino, alkoxy, or aryloxy, wherein $R^{20}$, $R^{21}$ and $R^{22}$ are each independently alkyl, aryl, halo, hydroxy or alkoxy;

$R^7$ is H, alkyl, aryl, amino, alkoxy, cyano or acyl; and $R^8$ is H, alkyl or aryl;

comprising:

(a) treating a compound of the formula:

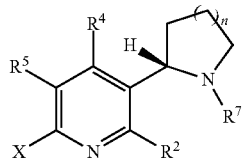

(IV)

wherein X is halo with optionally but preferably a base, optionally but preferably in the presence of an alcohol (e.g., $R^8OH$), and optionally but preferably with a metal catalyst, to form a compound of Formula III.

A third aspect of the present invention is a method of making a compound of Formula III

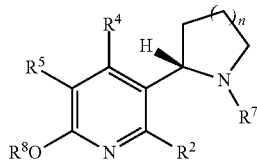

(III)

wherein:

n is 0, 1, 2 or 3;

$R^2$, $R^4$ and $R^5$ are each independently H, alkyl, aryl, heteroaryl, alkenyl, alkynyl, $SiR^{20}R^{21}R^{22}$, $SnR^{20}R^{21}R^{22}$, halo, amino, alkoxy, or aryloxy, wherein $R^{20}$, $R^{21}$ and $R^{22}$ are each independently alkyl, aryl, halo, hydroxy or alkoxy;

$R^7$ is H, alkyl, aryl, amino, alkoxy, cyano or acyl; and $R^8$ is H, alkyl or aryl;

comprising:

(a) metalating a compound of the formula:

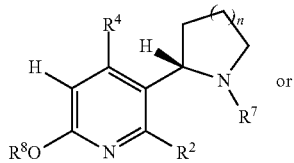

(IIIa)

or

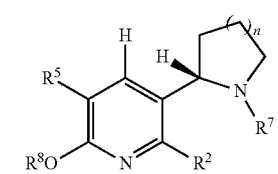

(IIIb)

with a metal base to form an organometallic intermediate compound; and then (b) reacting the organometallic intermediate compound with an electrophile to produce a compound of Formula III.

A fourth aspect of the present invention is a method of making compounds of Formula III:

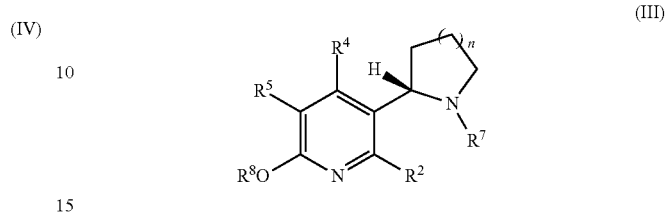

(III)

wherein:

n is 0, 1, 2 or 3;

$R^2$, $R^4$ and $R^5$ are each independently H, alkyl, aryl, heteroaryl, alkenyl, alkynyl, $SiR^{20}R^{21}R^{22}$, $SnR^{20}R^{21}R^{22}$, halo, amino, alkoxy, or aryloxy, wherein $R^{20}$, $R^{21}$ and $R^{22}$ are each independently alkyl, aryl, halo, hydroxy or alkoxy;

$R^7$ is H, alkyl, aryl, amino, alkoxy, cyano or acyl; and $R^8$ is H, alkyl or aryl;

comprising:

(a) treating a compound of the formula:

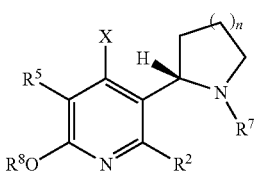

(IIIc)

wherein X is halo, with a nucleophilic cross-coupling reagent, and optionally but preferably a metal catalyst, to form a compound of the Formula III.

A fifth aspect of the present invention is a method of making compounds of Formula Ia

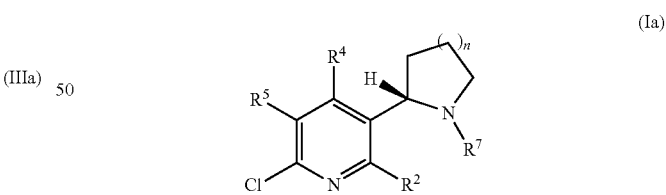

(Ia)

wherein:

n is 0, 1, 2 or 3;

$R^2$ is selected from the group consisting of H, alkyl, aryl, alkoxy and halo, preferably H;

$R^4$ and $R^5$ are independently selected from the group consisting of alkyl, aryl, heteroaryl, alkenyl, alkynyl, alkoxy, aryloxy, halo, amino, $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy; and $R^7$ is H, alkyl, aryl, amino, alkoxy, cyano or acyl;

comprising:

(a) treating a compound of the formula:

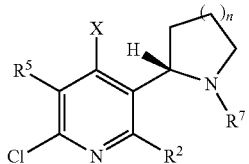

(Ic)

wherein X is halo, with a nucleophilic cross-coupling reagent, and a metal catalyst to form a compound of the Formula Ia.

A sixth aspect of the present invention is a method of making a compound of Formula VI:

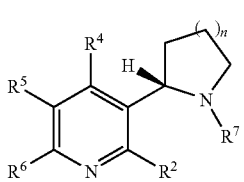

(VI)

wherein:

n is 0, 1, 2 or 3;

$R^2$ and $R^5$ are each independently H, alkyl, aryl, heteroaryl, alkylamino, halo, alkoxy, or aryloxy, $SiR^{20}R^{21}R^{22}$, $SnR^{20}R^{21}R^{22}$, halo, or alkoxy wherein $R^{20}$, $R^{21}$ and $R^{22}$ are each independently alkyl, aryl, halo, hydroxy, alkoxy, or aryloxy;

$R^4$ is H, alkyl, aryl, heteroaryl, alkenyl, or alkynyl; $SiR^{20}R^{21}R^{22}$, $SnR^{20}R^{21}R^{22}$, halo, or alkoxy wherein $R^{20}$, $R^{21}$ and $R^{22}$ are each independently alkyl, aryl, halo, hydroxy, alkoxy, or aryloxy; and $R^6$ is alkyl, aryl, heteroaryl, alkylamino, halo, amino, dialkylamino, arylamino, diarylamino, alkenyl, alkynyl, or alkoxy;

$R^7$ is H, alkyl, aryl, amino, alkoxy, aryloxy, cyano or acyl;

comprising:

(a) treating a compound of the formula:

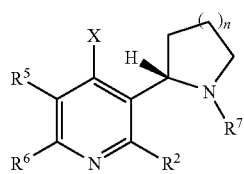

(V)

wherein:

X is an alkyltin, alkylsilane, alkylborane, boronic acid, or a metal halide, with a cross-coupling partner and a metal catalyst to form a compound of the Formula VI.

A seventh aspect of the present invention is a method of making a compound of Formula VI:

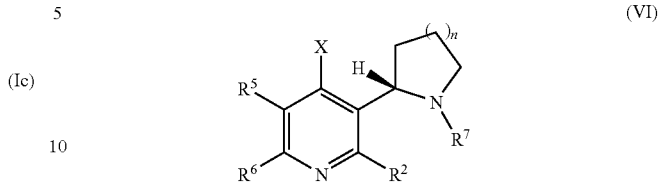

(VI)

wherein:

n is 0, 1, 2 or 3;

$R^2$ and $R^5$ are each independently H, alkyl, aryl, heteroaryl, alkylamino, halo, alkoxy, or aryloxy, $SiR^{20}R^{21}R^{22}$, $SnR^{20}R^{21}R^{22}$, halo, or alkoxy wherein $R^{20}$, $R^{21}$ and $R^{22}$ are each independently alkyl, aryl, halo, hydroxy, alkoxy, or aryloxy;

$R^4$ is H, alkyl, aryl, heteroaryl, alkenyl, or alkynyl; $SiR^{20}R^{21}R^{22}$, $SnR^{20}R^{21}R^{22}$, halo or alkoxy wherein $R^{20}$, $R^{21}$ and $R^{22}$ are each independently alkyl, aryl, halo, hydroxy, alkoxy, or aryloxy; and $R^6$ is alkyl, aryl, heteroaryl, alkylamino, halo, amino, dialkylamino, arylamino, diarylamino, alkenyl, alkynyl, or alkoxy;

$R^7$ is H, alkyl, aryl, amino, alkoxy, aryloxy, cyano or acyl;

comprising:

(a) treating a compound of Formula IV:

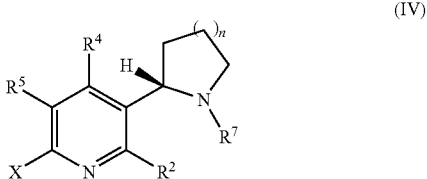

(IV)

wherein X is halo, preferably iodo, with: an amine, optionally but preferably a base and optionally but preferably a metal catalyst; or a nucleophilic cross-coupling reagent and optionally but preferably a metal catalyst, to form a compound of the Formula VI.

A further aspect of the present invention is a compound of Formula A:

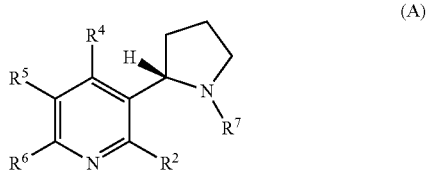

(A)

wherein:

$R^2$ is selected from the group consisting of H, alkyl, aryl, alkoxy and halo, $R^4$ is selected from the group consisting of alkyl, aryl, heteroaryl, alkenyl, alkynyl, alkoxy, aryloxy, halo, $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy; and $R^5$ and $R^6$ is each independently selected from the group consisting of H, alkyl, aryl, heteroaryl, alkenyl, alkynyl, alkoxy, aryloxy, halo, $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy;

$R^7$ is H, alkyl aryl, amino, alkoxy, cyano or acyl;

and pharmaceutically acceptable salts and prodrugs thereof.

A further aspect of the present invention is a compound of Formula A:

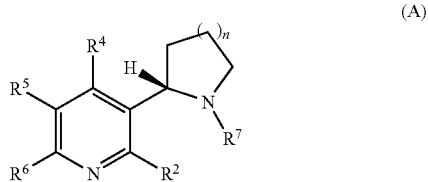

(A)

wherein:

n is 0, 1, 2 or 3;

$R^2$ is selected from the group consisting of H, alkyl, aryl, alkoxy and halo, $R^4$, $R^5$ and $R^6$ is selected from the group consisting of H, alkyl, aryl, heteroaryl, alkenyl, alkynyl, alkoxy, aryloxy, halo, $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy;

$R^7$ is H, alkyl, aryl, amino, alkoxy, cyano or acyl;

subject to the proviso that either $R^4$ and $R^5$, or $R^5$ and $R^6$, together form a fused ring, and pharmaceutically acceptable salts and prodrugs thereof.

A further aspect of the present invention is a composition comprising a compound as described herein in a pharmaceutically acceptable carrier.

A further aspect of the present invention is a composition comprising a compound as described herein in an insecticidal carrier.

A further aspect of the present invention is a method of treating a neurological disorder in a subject in need thereof, comprising administering said subject an active compound as described herein in an amount effective to treat said disorder.

A further aspect of the present invention is a method of killing insects, comprising administering to insects a compound as described herein in an insecticidally effective amount.

A further aspect of the present invention is a method of facilitating cessation of smoking such as cigarette smoking in a human subjects, comprising administering said subject an active compound as described herein in an amount effective to facilitate cessation of smoking in said subject (e.g., an amount effective to reduce the subject's desire or craving for smoking).

A further aspect of the present invention is the use of a compound or active compound as described herein for the preparation of a medicament for the treatment of a disease or disorder as described herein.

DETAILED DESCRIPTION OF THE PREFERRED EMBODIMENTS

"Alkyl" as used herein refers to straight or branched chain or cyclo alkyl groups having in the range of about 1 up to 12 carbon atoms. "Lower alkyl" refers to straight or branched chain alkyl groups having in the range of about 1 up to 4 carbon atoms. Alkyl and loweralkyl may be substituted or unsubstituted unless specified otherwise herein; "substituted alkyl" refers to alkyl or lower alkyl groups further bearing one or more substituents such as hydroxy, alkoxy (of a lower alkyl group), aryl, mercapto (of a lower alkyl group), halogen, trifluoromethyl, cyano, nitro, amino, carboxyl, carbamate, sulfonyl, sulfonamide, and the like. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

"Alkoxy" as used herein refers to a compound of the formula RO—, where R is alkyl or loweralkyl (which may be substituted or unsubstituted unless specified otherwise) as given above.

"Alkenyl" refers to straight or branched chain hydrocarbyl groups such as alkyl or loweralkyl groups as described above (and which may be substituted or unsubstituted unless specified otherwise) and having at least one carbon-carbon double bond.

"Alkynyl" refers to straight or branched chain hydrocarbyl radicals such as alkyl or loweralkyl groups as described above (and which may be substituted or unsubstituted unless specified otherwise) and having at least one carbon-carbon triple bond.

"Halo" refers to fluoro, chloro, bromo or iodo.

"Aryl," as used herein, refers to a monocyclic carbocyclic ring system or a bicyclic carbocyclic fused ring system having one or more aromatic rings. Examples of aryl include but are not limited to azulenyl, indanyl, indenyl, naphthyl, phenyl, tetrahydronaphthyl, and the like. The aryl groups may be substituted or unsubstituted unless specified otherwise and when substituted can for example be substituted with 1, 2, 3, 4, or 5 substituents independently selected from alkyl, alkenyl, alkenyloxy, alkoxy, alkoxyalkoxy, alkoxycarbonyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, NR'R" (wherein R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Aryloxy" as used herein refers to a compound of the formula RO—, where R is aryl (which may be substituted or unsubstituted unless specified otherwise) as given above.

"Acyl" as used herein refers to a group of the formula —C(O)—R, radical, where R is a R', OR', or NR'R", where R' and R" are any suitable substituent such as alkyl, aryl, arylalkyl, etc. (for example, an acetyl group, a propionyl group, a butyroyl group, a benzoyl group, or an alkylbenzoyl group, etc.).

"Alkylidene chain" as used herein refers to a difunctional organic group which can be linear, branched, and/or cyclic or polycyclic (e.g., containing 2 or 3 to 8, 12 or 16 carbon atoms), and which difunctional organic group may be substituted or unsubstituted, and which may be saturated or unsaturated, and which may optionally contain one, two or three heteroatoms selected from the group consisting of N, O, Si, and S. Examples include but are not limited to alkylene, alkenylene, alkynylene, arylene, alkarylene, and aralkylene. See, e.g., U.S. Pat. No. 6,946,533.

"Fused ring" as used herein with respect to two substituents (e.g., $R^4$ and $R^5$, or $R^5$ and $R^6$, together forming a fused ring, refers to the two groups together forming an alkylidene chain as described herein. Fused rings may be aromatic or aliphatic. Examples of such fused rings include, but are not limited to:

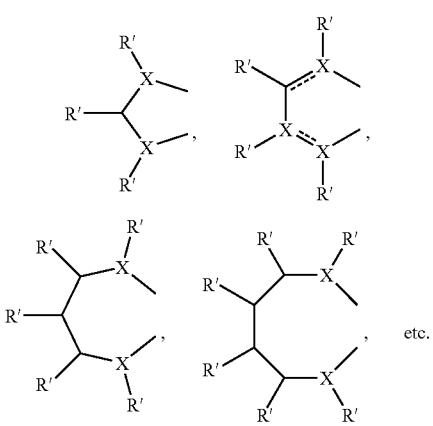

wherein each X is independently selected from the group consisting of C(R'), N, O, SiR', and S, and wherein each R' is independently selected from the group consisting of H, alkyl, aryl, heteroaryl, alkenyl, alkynyl, alkoxy, aryloxy, and halo, or an adjacent pair of R's may in turn form an additional fused ring as defined herein (to in turn form, together with the parent ring, a three or four fused ring system), and/or one or two adjacent pairs of R's may together form a covalent bond.

Specific examples of fused rings as set forth above include, but are not limited to:

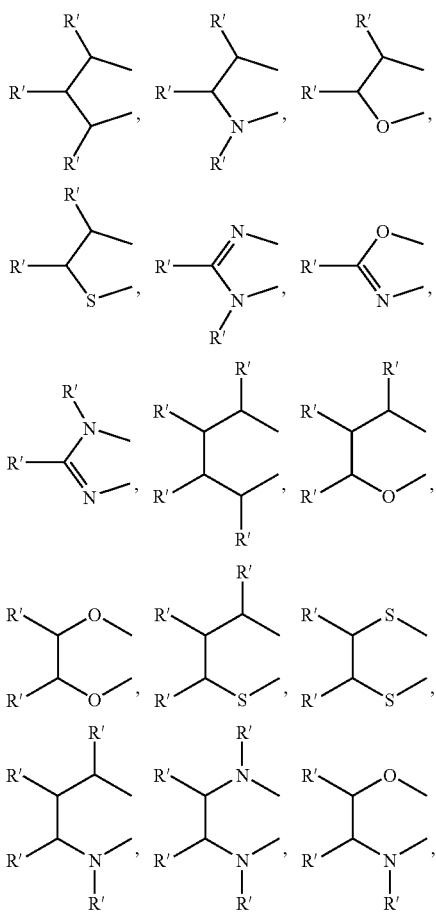

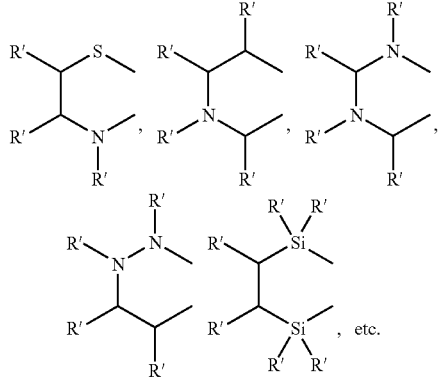

wherein each R' is independently selected from the group consisting of H, alkyl, aryl, heteroaryl, alkenyl, alkynyl, alkoxy, aryloxy, and halo, or an adjacent pair of R's may in turn form an additional fused ring as defined herein (to in turn form, together with the parent ring, a three or four fused ring system), and/or one or two adjacent pairs of R's may together form a covalent bond (e.g., to form an aromatic fused ring).

"Nucleophilic cross-coupling reagent" as used herein may be any suitable cross coupling reagent that provides the desired substituent (e.g. $R^4$, $R^6$, etc). Examples include but are not limited to, $R^4SnR^{20}R^{21}R^{22}$, $R^4SiR^{20}R^{21}R^{22}$, $R^4BR^{23}R^{24}$, $R^4MgX$, and $R^4ZnX$, wherein $R^{20}$, $R^{21}$ and $R^{22}$ are each independently alkyl, aryl, halo, hydroxy or alkoxy, and X is halo; or $R^6SnR^{20}R^{21}R^{22}$, $R^6SiR^{20}R^{21}R^{22}$, $R^6BR^{23}R^{24}$, $R^6MgX$, and $R^6ZnX$, wherein $R^{20}$, $R^{21}$ and $R^{22}$ are each independently alkyl, aryl, halo, hydroxy or alkoxy, and X is halo.

"Metal catalyst" as used herein may be any suitable metal catalyst, including but not limited to complexes of Pd, Ni, Cu, Rh, Pt, Fe, etc.

"Base" as used herein with respect to metalations may be any suitable metal base as discussed below. "Base" as used herein with respect to cross-coupling reactions may be any suitable base, including but not limited to, $K_2CO_3$, $Cs_2CO_3$, sodium tert-butoxide, etc.

"Metal base" as used herein base may be an alkyllithium base, an example of which is the basic reagent composed of BuLi and $Me_2N(CH_2)_2OLi$ known as BuLi-LiDMAE and described in, for example, P. Gros, *J. Org. Chem.* 67, 234-237 (2002) and sometimes referred to as Base A herein. Another suitable base for carrying out the methods of the present invention is lithium di-tert-butyltetramethylpiperidinozincate (TMP-zincate), described in, for example, Y. Kondo, *J. Am. Chem. Soc.* 121, 3539-3540, and sometimes referred to as Base B herein.

"Cross-coupling partner" as used herein includes organo halides (e.g., $R^4X$ where $R^4$ is the group to be added and X is halo), and the corresponding sulfonates, phosphonates, tosylates and the like which can serve as an electrophile.

"Pharmaceutically acceptable salt" as used herein is a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, .gamma.-hydroxybutyrates, glycollates, tartrates, methane-sulfonates, propanesulfonates, naphthalene-1-sulfonates, naphthalene-2-sulfonates, and mandelates.

"Pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

"Treat" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Halogenating agent" as used herein may be any suitable halogenating agent, including but not limited to $I_2$, $C_2Cl_6$, $I(CH_2)_2Cl$, $Br(CCl_2)_2Br$, N-bromosuccinimide, $Br_2$, N-iodosuccinimide, $CCl_4$, 1,3-dichloro-5,5-dimethylhydantoin, etc.

"Electrophile" as used herein is any reagent that adds the desired substituent to another intermediate as described herein by an addition or substitution reaction. Examples include, but are not limited to, alkyl halides, aldehydes, ketones, esters, amides, carbonates, etc., such as compounds of the formulas:

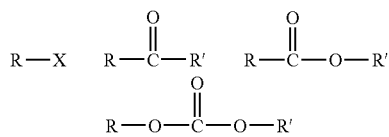

where R is the group to be added (e.g. $R^2$, $R^4$, $R^5$, etc), X is halo or sulfonate, and R' is any suitable substituent such as H, alkyl, aryl, etc., with OR' generally serving as a leaving group.

The disclosures of all United States patent references cited herein are to be incorporated herein by reference in their entirety.

Reactions of the present invention may be carried out in any suitable organic solvent, with the particular solvent chosen depending in part on the base chosen for the reaction. For example, reactions utilizing Base A are preferably carried out in a nonpolar aprotic solvent such as hexane or toluene. Reactions utilizing base B are preferably carried out in an etherial solvent such as tetrahydrofuran. The reactions may be conveniently carried out as "one pot" reactions if desired. The time and temperatures of the reactions are not critical, but may for example be from −80° C. to 100° C., and from 1 to 24 hours in duration.

Active compounds, intermediates and methods of making. As noted above, a first aspect of the present invention is a method for making a compound of Formula Ia:

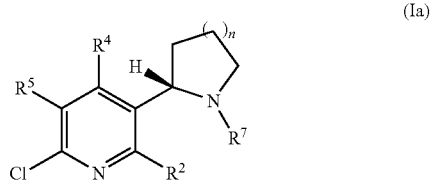

wherein:

n is 0, 1, 2 or 3;

$R^2$ is selected from the group consisting of H, alkyl, aryl, alkoxy and halo, preferably H;

$R^4$ and $R^5$ are independently selected from the group consisting of alkyl, aryl, heteroaryl, alkenyl, alkynyl, alkoxy, aryloxy, halo, amino, $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy; and $R^7$ is H, alkyl, aryl, amino, alkoxy, cyano or acyl.

The method comprises:

(a) metalating a compound of the formula IIa, IIb, IIc or IId:

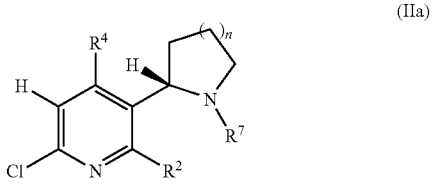

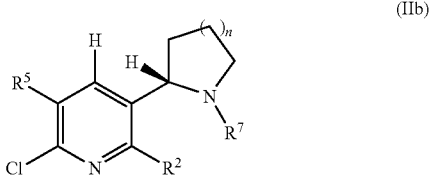

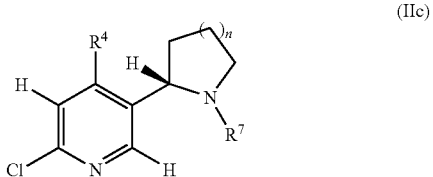

-continued

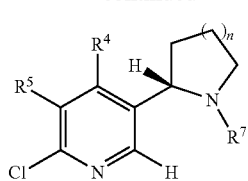
(IId)

with a metal base to form an organometallic intermediate compound; and then (b) reacting the organometallic intermediate compound with an electrophile to produce a compound of Formula Ia.

A second aspect of the present invention is a method of making a compound of Formula III:

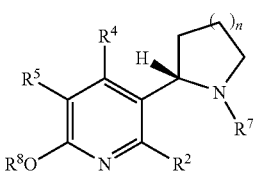
(III)

wherein:

n is 0, 1, 2 or 3;

$R^2$, $R^4$ and $R^5$ are each independently H, alkyl, aryl, heteroaryl, alkenyl, alkynyl, $SiR^{20}R^{21}R^{22}$, $SnR^{20}R^{21}R^{22}$, halo, amino, alkoxy, or aryloxy, wherein $R^{20}$, $R^{21}$ and $R^{22}$ are each independently alkyl, aryl, halo, hydroxy or alkoxy;

$R^7$ is H, alkyl, aryl, amino, alkoxy, cyano or acyl; and $R^8$ is H, alkyl or aryl.

The method comprises:

(a) treating a compound of the formula:

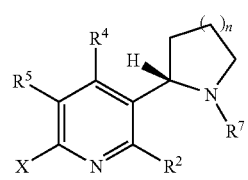
(IV)

wherein X is halo, preferably iodo, with an alcohol (e.g., $R^8OH$), a base and a metal catalyst to form a compound of Formula III.

A third aspect of the present invention is another method of making a compound of Formula III

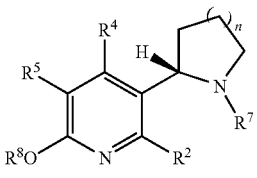
(III)

wherein:

n is 0, 1, 2 or 3;

$R^2$, $R^4$ and $R^5$ are each independently H, alkyl, aryl, heteroaryl, alkenyl, alkynyl, $SiR^{20}R^{21}R^{22}$, $SnR^{20}R^{21}R^{22}$, halo, amino, alkoxy, or aryloxy, wherein $R^{20}$, $R^{21}$ and $R^{22}$ are each independently alkyl, aryl, halo, hydroxy or alkoxy;

$R^7$ is H, alkyl, aryl, amino, alkoxy, cyano or acyl; and $R^8$ is H, alkyl or aryl.

The method comprises:

(a) metalating a compound of the formula:

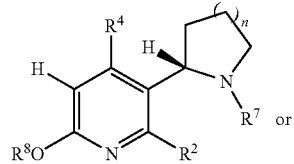
(IIIa)

or

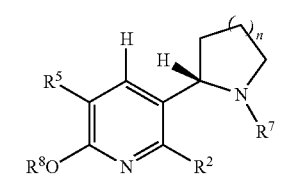
(IIIb)

with a metal base to form an organometallic intermediate compound; and then (b) reacting the organometallic intermediate compound with an electrophile to produce a compound of Formula III.

A fourth aspect of the present invention is a method of making compounds of Formula III

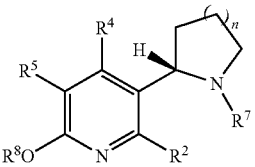
(III)

wherein:

n is 0, 1, 2 or 3;

$R^2$, $R^4$ and $R^5$ are each independently H, alkyl, aryl, heteroaryl, alkenyl, alkynyl, $SiR^{20}R^{21}R^{22}$, $SnR^{20}R^{21}R^{22}$, halo, amino, alkoxy, or aryloxy, wherein $R^{20}$, $R^{21}$ and $R^{22}$ are each independently alkyl, aryl, halo, hydroxy or alkoxy;

$R^7$ is H, alkyl, aryl, amino, alkoxy, cyano or acyl; and $R^8$ is H, alkyl or aryl.

The method comprises:

(a) treating a compound of the formula:

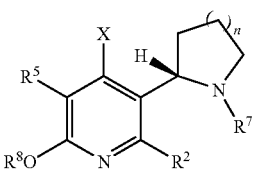
(IIIc)

wherein X is halo, preferably iodo, with a nucleophilic cross-coupling reagent and a metal catalyst to form a compound of the Formula III.

A fifth aspect of the present invention is another method of making a compound of Formula Ia.

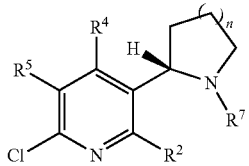

wherein:

n is 0, 1, 2 or 3;

$R^2$ is selected from the group consisting of H, alkyl, aryl, alkoxy and halo, preferably H;

$R^4$ and $R^5$ are independently selected from the group consisting of alkyl, aryl, heteroaryl, alkenyl, alkynyl, alkoxy, aryloxy, halo, amino $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy; and $R^7$ is H, alkyl, aryl, amino, alkoxy, cyano or acyl.

The method comprises:

(a) treating a compound of the formula:

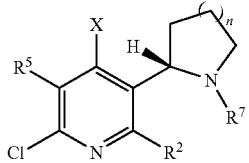

wherein X is halo, preferably iodo, with a nucleophilic cross-coupling reagent and a metal catalyst to form a compound of the Formula Ia.

A sixth aspect of the present invention is a method of making a compound of Formula VI

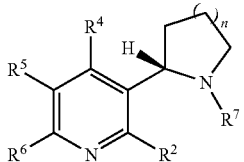

wherein:

n is 0, 1, 2 or 3;

$R^2$ and $R^5$ are each independently H, alkyl, aryl, heteroaryl, alkylamino, halo, alkoxy, or aryloxy, $SiR^{20}R^{21}R^{22}$, $SnR^{20}R^{21}R^{22}$, halo, or alkoxy wherein $R^{20}$, $R^{21}$ and $R^{22}$ are each independently alkyl, aryl, halo, hydroxy, alkoxy, or aryloxy;

$R^4$ is H, alkyl, aryl, heteroaryl, alkenyl, or alkynyl; $SiR^{20}R^{21}R^{22}$, $SnR^{20}R^{21}$, $R^{22}$, halo, or alkoxy wherein $R^{20}$, $R^{21}$ and $R^{22}$ are each independently alkyl, aryl, halo, hydroxy, alkoxy, or aryloxy; and $R^6$ is alkyl, aryl, heteroaryl, alkylamino, halo, amino, dialkylamino, arylamino, diarylamino, alkenyl, alkynyl, or alkoxy;

$R^7$ is H, alkyl, aryl, amino, alkoxy, aryloxy, cyano or acyl.

The method comprises:

(a) treating a compound of the formula:

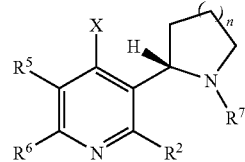

wherein:

X is an alkyltin, alkylsilane, alkylborane, boronic acid, or a metal halide, e.g., —$SnR^{20}R^{21}R^{22}$, —$SiR^{20}R^{21}R^{22}$, —$BR^{23}R^{24}$, —MgX, or —ZnX, preferably —$SnR^{20}R^{21}R^{22}$, wherein $R^{20}$, $R^{21}$, $R^{22}$, $R^{23}$, and $R^{24}$ are each independently alkyl, aryl, halo, hydroxy, alkoxy or aryloxy, with an appropriate organo halide ($R^4X$), or other cross-coupling partner and a metal catalyst to form a compound of the Formula VI.

A seventh aspect of the present invention is a method of making a compound of Formula VI.

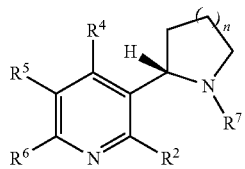

wherein:

n is 0, 1, 2 or 3;

$R^2$ and $R^5$ are each independently H, alkyl, aryl, heteroaryl, alkylamino, halo, alkoxy, or aryloxy, $SiR^{20}R^{21}R^{22}$, $SnR^{20}R^{21}R^{22}$, halo, or alkoxy wherein $R^{20}$, $R^{21}$ and $R^{22}$ are each independently alkyl, aryl, halo, hydroxy, alkoxy, or aryloxy;

$R^4$ is H, alkyl, aryl, heteroaryl, alkenyl, or alkynyl; $SiR^{20}R^{21}R^{22}$, $SnR^{20}R^{21}R^{22}$, halo, or alkoxy wherein $R^{20}R^{21}$ and $R^{22}$ are each independently alkyl, aryl, halo, hydroxy, alkoxy, or aryloxy; and $R^6$ is alkyl, aryl, heteroaryl, alkylamino, halo, amino, dialkylamino, arylamino, diarylamino, alkenyl, alkynyl, or alkoxy;

$R^7$ is H, alkyl, aryl, amino, alkoxy, aryloxy, cyano or acyl.

The method comprises:

(a) treating a compound of Formula IV:

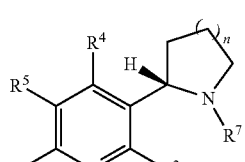

wherein X is halo, preferably iodo, with an amine, a base and a metal catalyst, or with a nucleophilic cross-coupling reagent and a metal catalyst to form a compound of the Formula VI.

A further aspect of the present invention is a compound of Formula A:

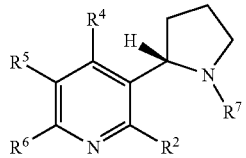

(A)

wherein:

$R^2$ is selected from the group consisting of H, alkyl, aryl, alkoxy and halo, $R^4$ is selected from the group consisting of alkyl, aryl, heteroaryl, alkenyl, alkynyl, alkoxy, aryloxy, halo, $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy; and $R^5$ and $R^6$ is each independently selected from the group consisting of H, alkyl, aryl, heteroaryl, alkenyl, alkynyl, alkoxy, aryloxy, halo, $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy;

$R^7$ is H, alkyl aryl, amino, alkoxy, cyano or acyl;

and pharmaceutically acceptable salts and prodrugs thereof.

A further aspect of the present invention is a compound of Formula A:

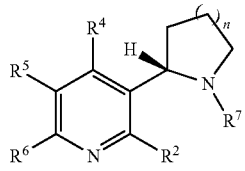

(A)

wherein:

n is 0, 1, 2 or 3;

$R^2$ is selected from the group consisting of H, alkyl, aryl, alkoxy and halo, $R^4$, $R^5$ and $R^6$ is selected from the group consisting of H, alkyl, aryl, heteroaryl, alkenyl, alkynyl, alkoxy, aryloxy, halo, $SiR^{20}R^{21}R^{22}$, $SnR^{20}R^{21}R^{22}$ wherein $R^{20}$, $R^{21}$ and $R^{22}$ are each independently alkyl, aryl, halo, hydroxy or alkoxy;

$R^7$ is H, alkyl aryl, amino, alkoxy, cyano or acyl;

subject to the proviso that either $R^4$ and $R^5$, or $R^5$ and $R^6$, together form a fused ring, and pharmaceutically acceptable salts and prodrugs thereof.

Examples of compounds that may be produced by the methods described herein include but are not limited to the following:

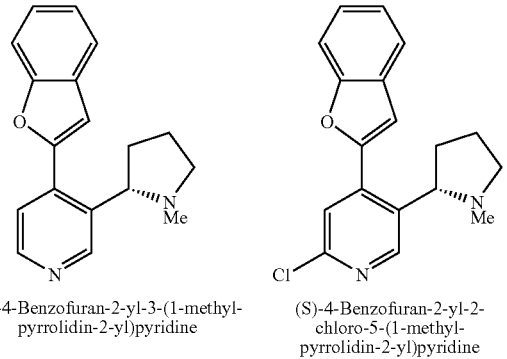

(S)-4-Benzofuran-2-yl-3-(1-methyl-pyrrolidin-2-yl)pyridine (S)-4-Benzofuran-2-yl-2-chloro-5-(1-methyl-pyrrolidin-2-yl)pyridine

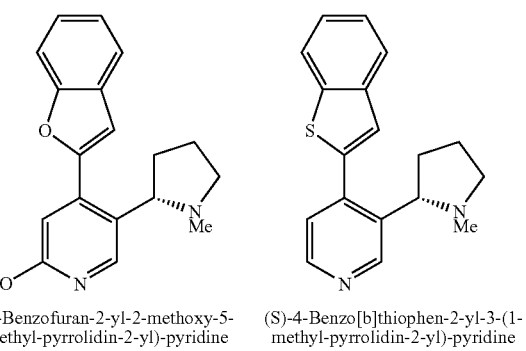

(S)-4-Benzofuran-2-yl-2-methoxy-5-(1-methyl-pyrrolidin-2-yl)-pyridine (S)-4-Benzo[b]thiophen-2-yl-3-(1-methyl-pyrrolidin-2-yl)-pyridine

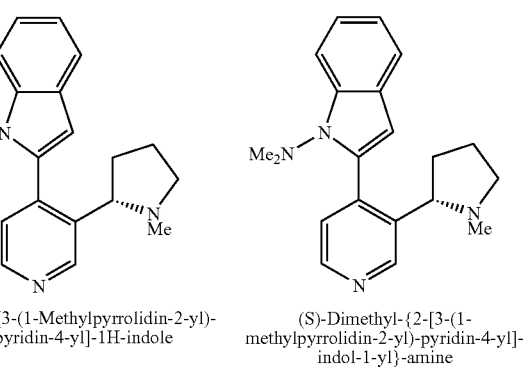

(S)-2-[3-(1-Methylpyrrolidin-2-yl)-pyridin-4-yl]-1H-indole (S)-Dimethyl-{2-[3-(1-methylpyrrolidin-2-yl)-pyridin-4-yl]-indol-1-yl}-amine

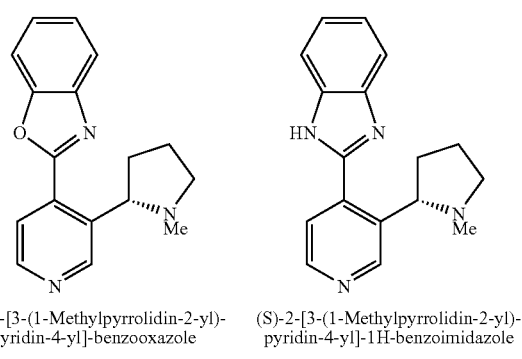

(S)-2-[3-(1-Methylpyrrolidin-2-yl)-pyridin-4-yl]-benzooxazole (S)-2-[3-(1-Methylpyrrolidin-2-yl)-pyridin-4-yl]-1H-benzoimidazole -continued

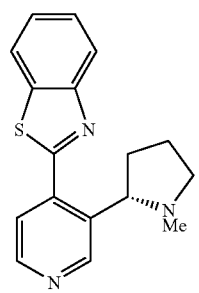

(S)-2-[3-(1-Methylpyrrolidin-2-yl)-
pyridin-4-yl]-benzothiazole

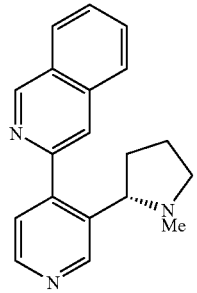

(S)-3-[3-(1-Methylpyrrolidin-2-yl)-
pyridin-4-yl]-isoquinoline

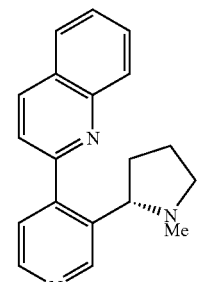

(S)-2-[3-(1-Methylpyrrolidin-2-yl)-
pyridin-4-yl]-quinoline

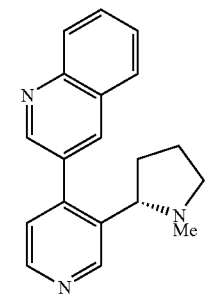

(S)-3-[3-(1-Methylpyrrolidin-2-yl)-
pyridin-4-yl]-quinoline

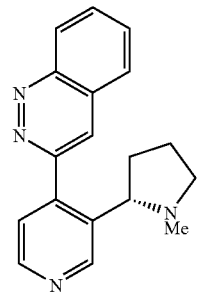

(S)-3-[3-(1-Methylpyrrolidin-2-yl)-
pyridin-4-yl]-cinnoline

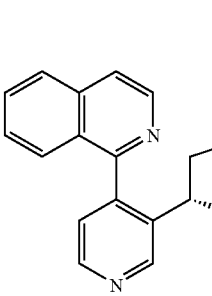

(S)-1-[3-(1-Methylpyrrolidin-2-yl)-
pyridin-4-yl]-isoquinoline

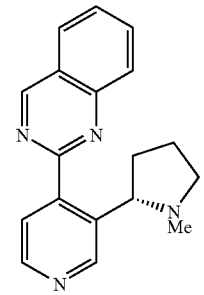

(S)-2-[3-(1-Methylpyrrolidin-2-yl)-
pyridin-4-yl]-quinazoline

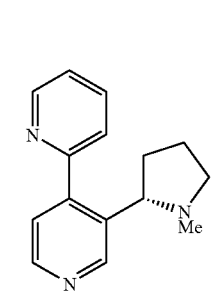

(S)-3'-(1-Methylpyrrolidin-2-yl)-
[2,4']bipyridinyl

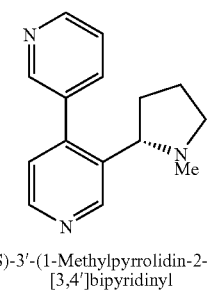

(S)-3'-(1-Methylpyrrolidin-2-yl)-
[3,4']bipyridinyl (S)-3-(1-Methylpyrrolidin-2-yl)-
[4,4']bipyridinyl -continued

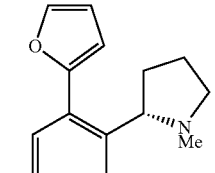

(S)-2-Chloro-4-furan-2-yl-5-
(1-methylpyrrolidin-2-yl)-pyridine

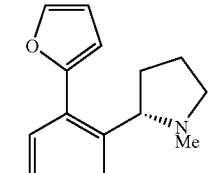

(S)-4-Furan-2-yl-2-methoxy-5-
(1-methylpyrrolidin-2-yl)-pyridine

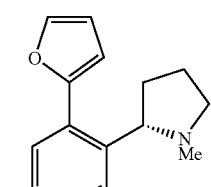

(S)-4-Furan-2-yl-2-methyl-5-
(1-methylpyrrolidin-2-yl)-pyridine

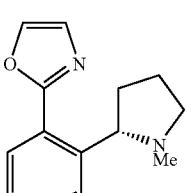

(S)-3-(1-Methylpyrrolidin-2-yl)-4-
oxazol-2-yl-pyridine

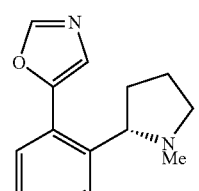

(S)-3-(1-Methylpyrrolidin-2-yl)-4
-oxazol-5-yl-pyridine

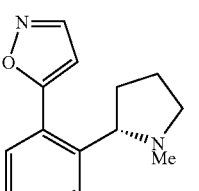

(S)-4-Isoxazol-5-yl-3-(1-
methylpyrrolidin-2-yl)-pyridine

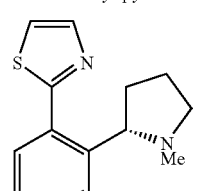

(S)-3-(1-Methylpyrrolidin-2-yl)-
4-thiazol-2-yl-pyridine

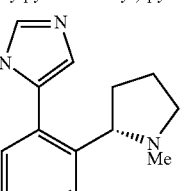

(S)-4-(3H-Imidazol-4-yl)-3-(1-
methylpyrrolidin-2-yl)-pyridine

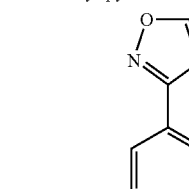

(S)-4-Isoxazol-3-yl-3-
(1-methylpyrrolidin-2-yl)-pyridine

Fused ring compounds. The present invention further provides methods of making fused ring compounds, which may be carried out in accordance with the following general scheme, in which XV is converted to give the fused bicyclic structure XVIII.

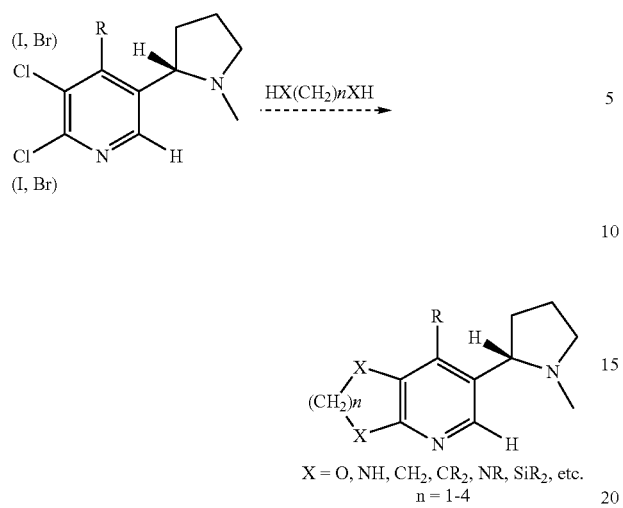

X = O, NH, CH₂, CR₂, NR, SiR₂, etc.
n = 1-4

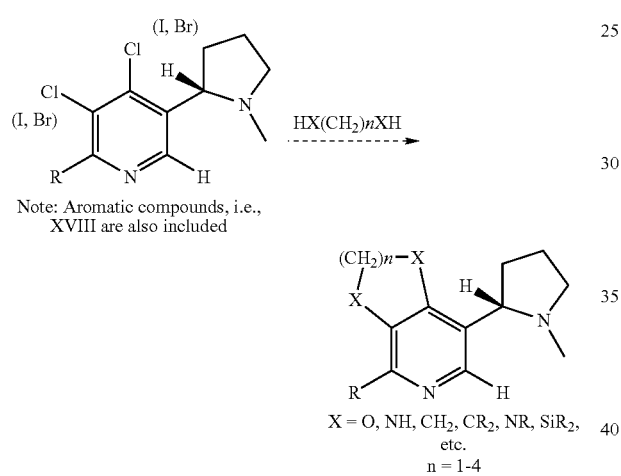

Note: Aromatic compounds, i.e., XVIII are also included

X = O, NH, CH₂, CR₂, NR, SiR₂, etc.
n = 1-4

A specific example of the foregoing reactions is as follows:

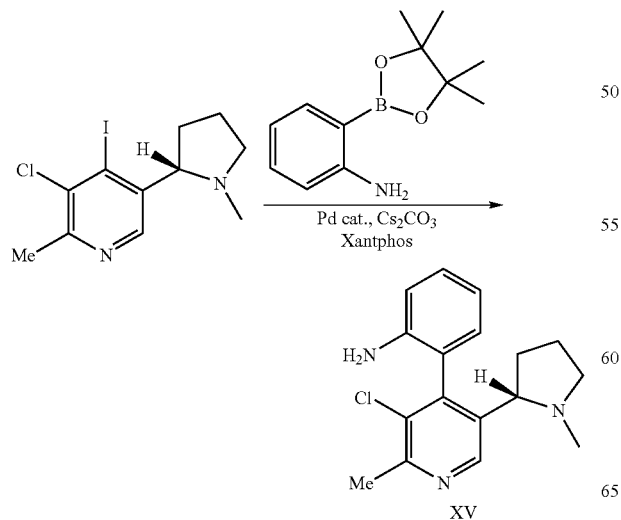

XV

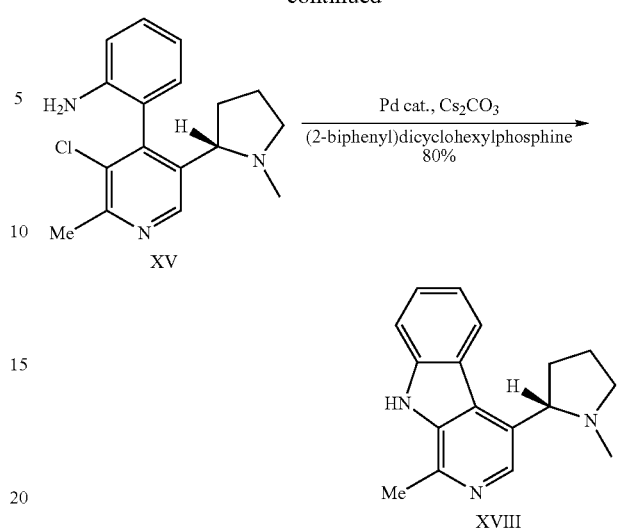

XVIII

Specific examples of fused ring compounds that can be made by the methods of the present invention include, but are not limited to:

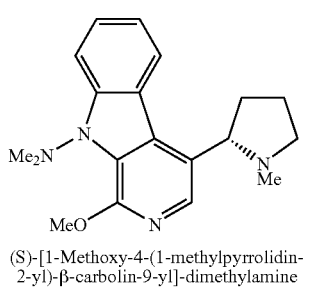

(S)-1-Chloro-4-(1-methylpyrrolidin-2-yl)-9H-β-carboline (S)-1-Methoxy-4-(1-methylpyrrolidin-2-yl)-9H-β-carboline

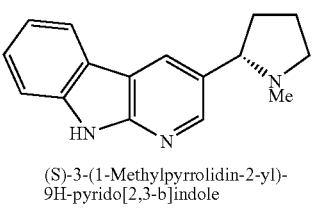

(S)-[1-Methoxy-4-(1-methylpyrrolidin-2-yl)-β-carbolin-9-yl]-dimethylamine (S)-3-(1-Methylpyrrolidin-2-yl)-9H-pyrido[2,3-b]indole

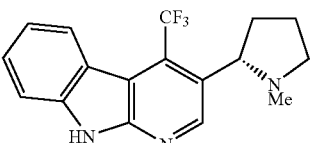

(S)-3-(1-Methylpyrrolidin-2-yl)-4-trifluoromethyl-9H-pyrido[2,3-b]indole

-continued

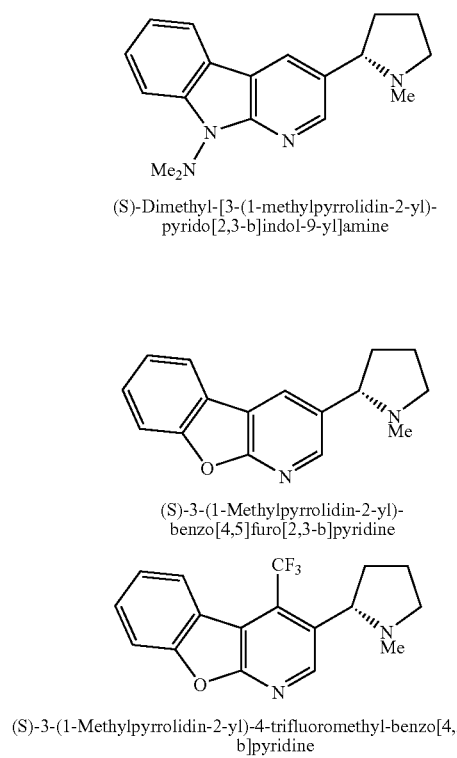

(S)-Dimethyl-[3-(1-methylpyrrolidin-2-yl)-pyrido[2,3-b]indol-9-yl]amine

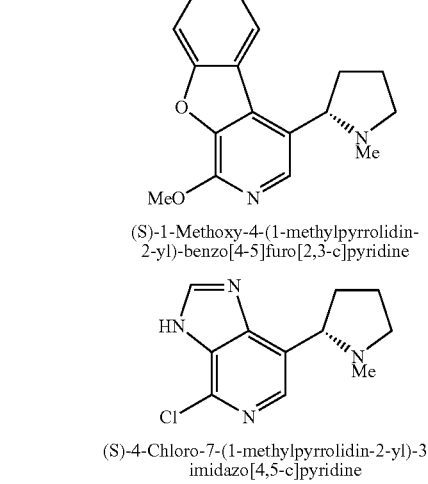

(S)-3-(1-Methylpyrrolidin-2-yl)-benzo[4,5]furo[2,3-b]pyridine (S)-3-(1-Methylpyrrolidin-2-yl)-4-trifluoromethyl-benzo[4,5]furo[2,3-b]pyridine (S)-1-Methoxy-4-(1-methylpyrrolidin-2-yl)-benzo[4-5]furo[2,3-c]pyridine (S)-4-Chloro-7-(1-methylpyrrolidin-2-yl)-3H-imidazo[4,5-c]pyridine

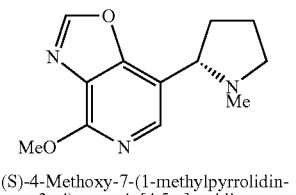

(S)-4-Methoxy-7-(1-methylpyrrolidin-2-yl)-oxazolo[4,5-c]pyridine

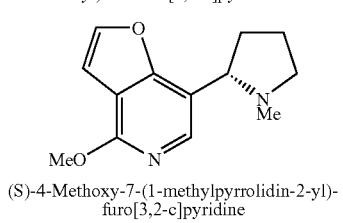

(S)-4-Methoxy-7-(1-methylpyrrolidin-2-yl)-furo[3,2-c]pyridine

-continued

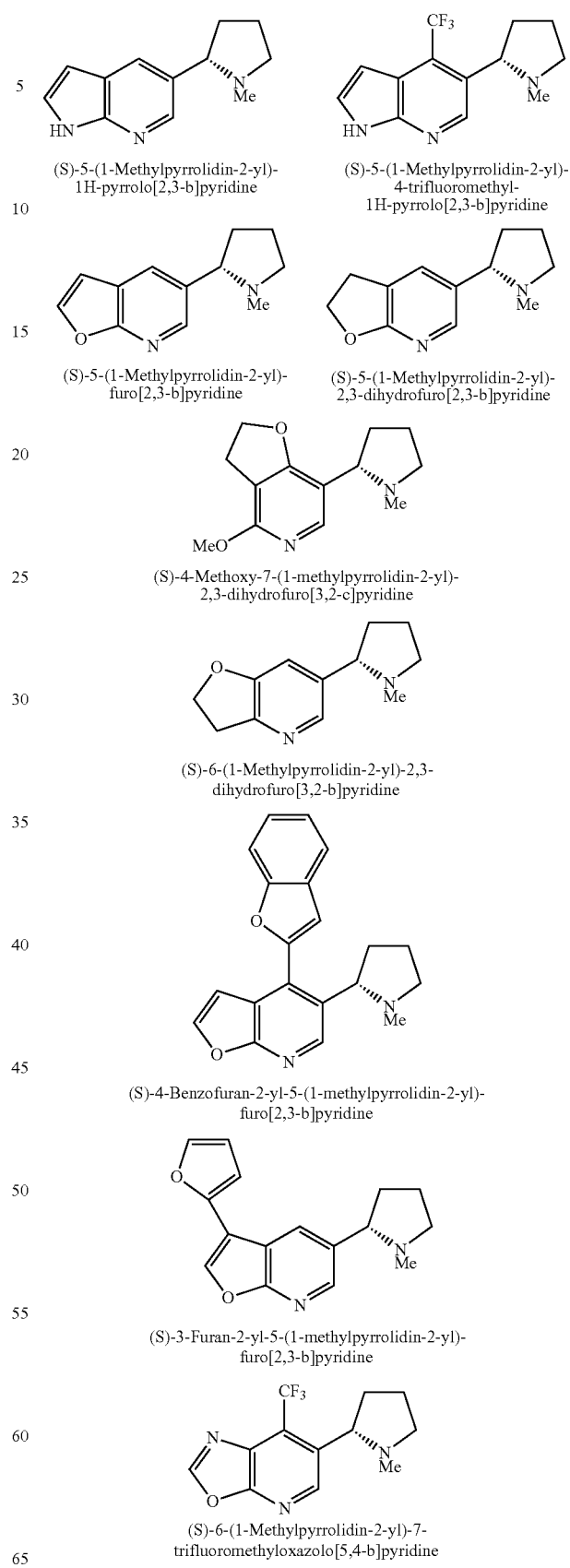

(S)-5-(1-Methylpyrrolidin-2-yl)-1H-pyrrolo[2,3-b]pyridine (S)-5-(1-Methylpyrrolidin-2-yl)-4-trifluoromethyl-1H-pyrrolo[2,3-b]pyridine (S)-5-(1-Methylpyrrolidin-2-yl)-furo[2,3-b]pyridine (S)-5-(1-Methylpyrrolidin-2-yl)-2,3-dihydrofuro[2,3-b]pyridine (S)-4-Methoxy-7-(1-methylpyrrolidin-2-yl)-2,3-dihydrofuro[3,2-c]pyridine (S)-6-(1-Methylpyrrolidin-2-yl)-2,3-dihydrofuro[3,2-b]pyridine (S)-4-Benzofuran-2-yl-5-(1-methylpyrrolidin-2-yl)-furo[2,3-b]pyridine (S)-3-Furan-2-yl-5-(1-methylpyrrolidin-2-yl)-furo[2,3-b]pyridine (S)-6-(1-Methylpyrrolidin-2-yl)-7-trifluoromethyloxazolo[5,4-b]pyridine

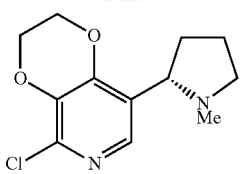

(S)-5-Chloro-8-(1-methylpyrrolidin-2-yl)-
2,3-dihydro-[1,4]dioxino[2,3-c]pyridine

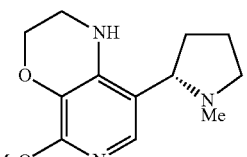

(S)-5-Methoxy-8-(1-methylpyrrolidin-2-yl)-
2,3-dihydro-1H-pyrido[3,4-b][1,4]oxazine

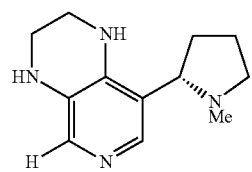

(S)-8-(1-Methylpyrrolidin-2-yl)-
1,2,3,4-tetrahydro-pyrido[3,4-b]pyrazine

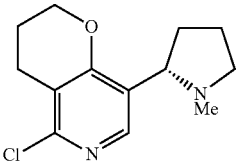

(S)-5-Chloro-8-(1-methylpyrrolidin-2-yl)-
3,4-dihydro-2H-pyrano[3,2-c]pyridine

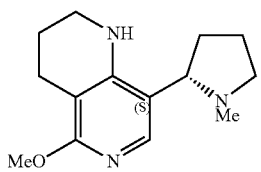

(S)-5-Methoxy-8-(1-methylpyrrolidin-2-yl)-
1,2,3,4-tetrahydro-[1,6]naphthyridine

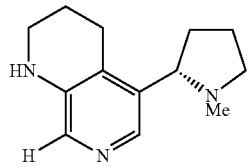

(S)-5-(1-Methylpyrrolidin-2-yl)-1,2,3,4-
tetrahydro-[1,7]naphthyridine

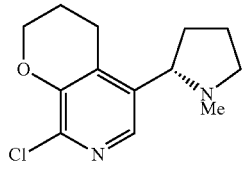

(S)-8-Chloro-5-(1-methylpyrrolidin-2-yl)-
3,4-dihydro-2H-pyrano[2,3-c]pyridine

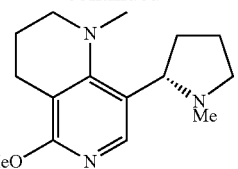

(S)-5-Methoxy-1-methyl-8-(1-methylpyrrolidin-2-yl)-
1,2,3,4-tetrahydro-[1,6]naphthyridine

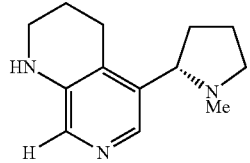

(S)-5-(1-Methylpyrrolidin-2-yl)-
1,2,3,4-tetrahydro-[1,7]naphthyridine

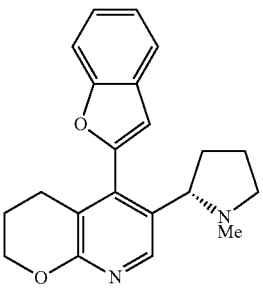

(S)-5-Benzofuran-2-yl-6-(1-methylpyrrolidin-2-yl)-
3,4-dihydro-2H-pyrano[2,3-b]pyridine

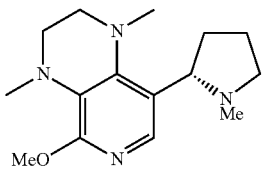

(S)-5-Methoxy-1,4-dimethyl-8-(1-methylpyrrolidin-2-yl)-
1,2,3,4-tetrahydro-pyrido[3,4-b]pyrazine

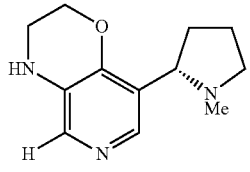

(S)-8-(1-Methylpyrrolidin-2-yl)-
3,4-dihydro-2H-pyrido[4,3-b][1,4]oxazine

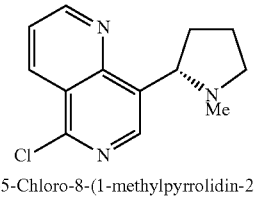

(S)-5-Chloro-8-(1-methylpyrrolidin-2-yl)-
[1,6]naphthyridine

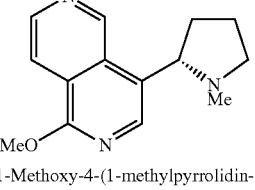

(S)-1-Methoxy-4-(1-methylpyrrolidin-2-yl)-
[2,6]naphthyridine

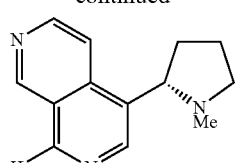

(S)-4-(1-Methylpyrrolidin-2-yl)-
[2,7]naphthyridine

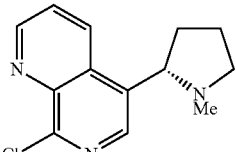

(S)-8-Chloro-5-(1-methylpyrrolidin-2-yl)-
[1,7]naphthyridine

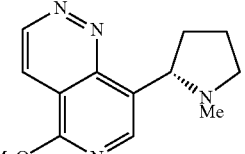

(S)-5-Methoxy-8-(1-methylpyrrolidin-2-yl)-
pyrido[4,3-c]pyridazine

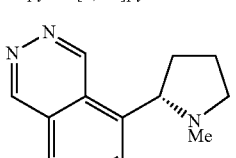

(S)-8-(1-Methylpyrrolidin-2-yl)-
pyrido[3,4-d]pyridazine

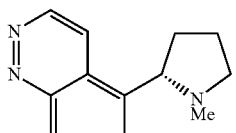

(S)-8-Chloro-5-(1-methylpyrrolidin-2-yl)-
pyrido[3,4-c]pyridazine

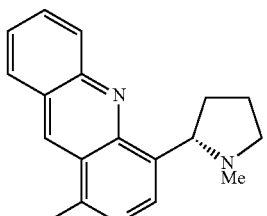

(S)-1-Methoxy-4-(1-methylpyrrolidin-2-yl)-
benzo[b][1,6]naphthyridine

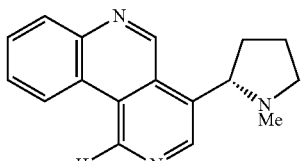

(S)-4-(1-Methylpyrrolidin-2-yl)-
benzo[c][2,6]naphthyridine

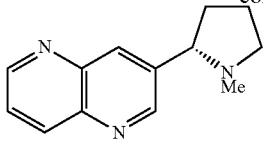

(S)-3-(1-Methylpyrrolidin-2-yl)-
[1,5]naphthyridine

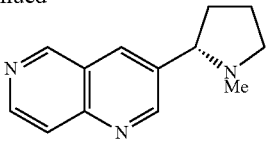

(S)-3-(1-Methylpyrrolidin-2-yl)-
[1,6]naphthyridine

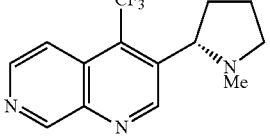

(S)-3-(1-Methylpyrrolidin-2-yl)-
4-trifluoromethyl-
[1,7]naphthyridine

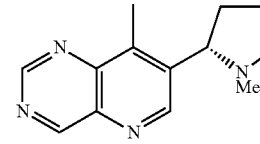

(S)-8-Methyl-7-(1-
methylpyrrolidin-2-yl)-pyrido[3,2-
d]pyrimidine

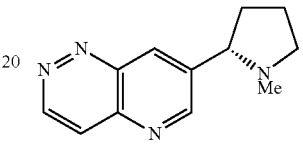

(S)-7-(1-Methylpyrrolidin-2-yl)-
pyrido[3,2-c]pyridazine

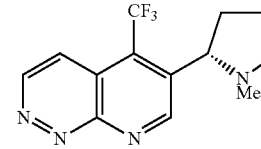

(S)-6-(1-Methylpyrrolidin-2-yl)-
5-trifluoromethyl-
pyrido[2,3-c]pyridazine

Salts and prodrugs of the foregoing are also examples of active compounds of the present invention.

Pharmaceutical formulations. The active compounds described above (including the salts and prodrugs thereof) may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible-with-any other ingredients in the formulation and must not be deleterious to the patient. The carrier may be a solid or a liquid, or both, and is preferably formulated with the compound as a unit-dose formulation, for example, a tablet, which, may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets; each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate, which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to, the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension:

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds (including their salts or prodrugs), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Subjects and treatment. Subjects that may be treated with the compounds of the invention to treat disorders or diseases as described above include both human subjects and animal subjects (e.g., dogs, cats, horses, cattle, monkeys, etc.) for veterinary purposes.

Compounds of the invention as described herein are useful as acetylcholine receptor modulating compounds and are useful as pharmacologically and pharmaceutically active compounds, including compounds useful for the treatment of neurological disorders such as Parkinson's disease, Alzheimer's disease, motor dysfunction and cognitive impairment in human and animal subjects, as compounds for use as an alternative to nicotine as an aid to smoking cessation programs, as insecticides, etc. Compounds of the present invention are also useful as intermediates for making compounds having utilities such as described above.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 μmol/kg to 50 μmol/kg, and more preferably 22 μmol/kg and 33 μmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

The present invention is explained in greater detail in the following non-limiting Examples.

Examples 1-5

Regioselective Substitution of (S)-6-Chloronicotine

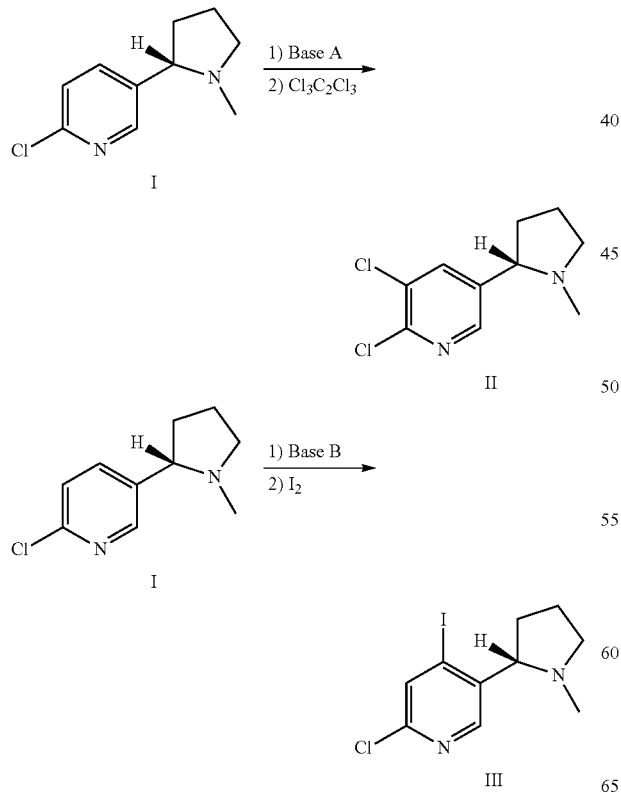

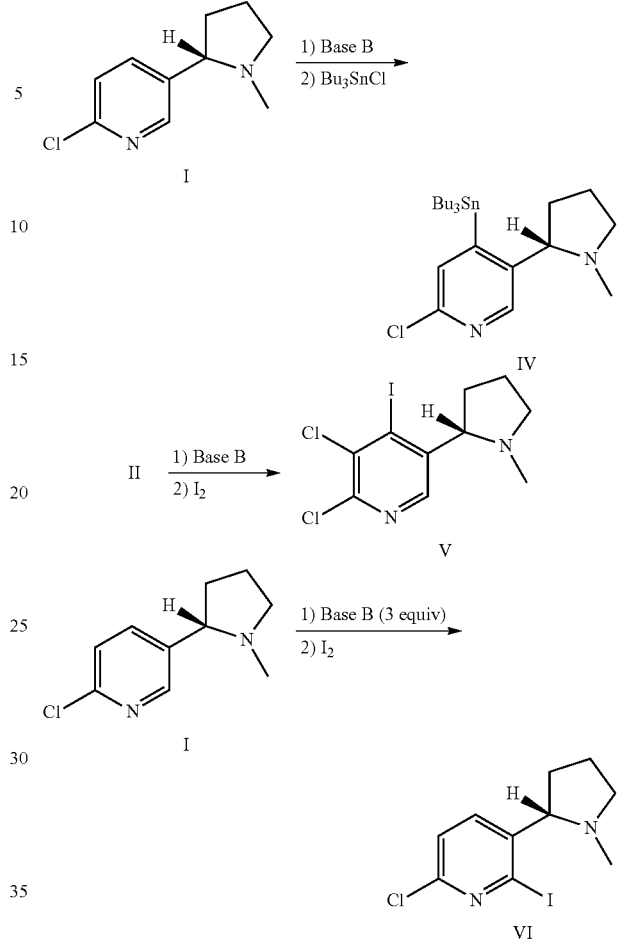

Base A: LiTMP

Base B: n-BuLi

Example 1

(S)-5,6-Dichloronicotine (II)

A solution of 2,2,6,6-tetramethylpiperidine (2.96 mmol, 500 μL, 1.1 equiv) in dry THF (3.0 mL) was treated with n-butyllithium (1.1 equiv) at −78° C. After 1 h at −78° C., (S)-6-chloronicotine (2.69 mmol, 530 mg, 1.0 equiv) was added dropwise. After 1 h at −78° C., a solution of hexachloroethane (3.23 mmol, 770 mg, 1.2 equiv) in dry THF (3.0 mL) was added to the mixture at −78° C. After 1 h at −78° C., the reaction was quenched with 3.0 mL of a saturated aqueous solution of sodium bicarbonate. The aqueous layer was extracted with methylene chloride (2×15 mL). The combined organic layers were dried over potassium carbonate. The solvent was removed by evaporation under reduced pressure to afford a light yellow oil. The product was purified by radial PLC (1% TEA/20% EtOAc/hexanes) to afford 542 mg (87% yield) of a light yellow oil: $[\alpha]^{24}_D$ −134 (c 0.8, $CH_2Cl_2$); IR (neat) 2968, 2781, 1547, 1420, 1392, 1329, 1149, 1042 $cm^{-1}$; $^1$H NMR (300 MHz, $CDCl_3$) 8.20 (d, 1H, J=2.4 Hz), 7.81 (d, 1H, J=2.4 Hz), 3.23 (dt, 1H, J=2.1, 8.4 Hz), 3.11 (t, 1H, J=8.4 Hz), 2.32 (q, 1H, J=8.4 Hz), 2.25-2.19 (m, 1H), 2.17 (s, 3H), 2.00-1.60 (m, 3H); $^{13}$C NMR (75 MHz, CDCl$_3$) δ 147.8, 146.9, 140.4, 137.9, 130.8, 67.6, 57.1, 40.6, 35.7, 22.9; HRMS calcd for C$_{10}$H$_{12}$Cl$_2$N$_2$ ([M+H]$^+$) 231.0456, found 231.0457.

Example 2

(S)-6-Chloro-4-iodonicotine (III)

(S)-6-Chloronicotine (200 mg, 1.02 mmol, 1.0 eq) was added to a solution of n-butyllithium (1.22 mmol, 1.2 eq) in THF (3 mL) at −78° C. After one hour, a solution of iodine (310 mg, 1.22 mmol, 1.2 eq) in THF (stored over 4 Å molecular sieves for 30 min) was added to the mixture. After 5 min at −78° C., the reaction was quenched with a saturated solution of sodium bicarbonate, and the mixture was warmed to room temperature. The mixture was extracted with methylene chloride (2×10 mL). The combined organic extracts were dried over sodium sulfate and filtered. The solvents were removed by evaporation and the product purified by radial PLC (1% TEA/20% EtOAc/hexanes) to afford 198 mg (60%) of product as white crystals, mp 100-101° C.: $[α]^{27}_D$ −141 (c 3.45, CH$_2$Cl$_2$); IR(CDCl$_3$) 2961, 2936, 2804, 1553, 1531, 1438, 1361, 1111, 827 cm$^{-1}$; $^1$H NMR (400 MHz, CDCl$_3$) δ 8.37 (s, 1H), 7.74 (s, 1H), 3.34 (t, J=8.4 Hz, 1H), 3.24 (dt, J=8.2 Hz, J=2.0 Hz, 1H), 2.44-2.30 (m, 2H), 2.20 (s, 3H), 1.92-1.76 (m, 2H), 1.50-1.40 (m, 1H); $^{13}$C NMR (100 MHz, CDCl$_3$) δ 149.7, 149.1, 141.0, 112.5, 71.7, 57.0, 40.7, 33.9, 22.9; HRMS Calcd for C$_{10}$H$_{12}$IN$_2$Cl [M+H]$^+$: 322.9812, found 322.9804.

Example 3

(S)-6-Chloro-4-(tributylstannyl)nicotine (IV)

(S)-6-Chloronicotine (100 mg, 0.51 mmol, 1.0 eq) was added to a solution of n-butyllithium (0.61 mmol, 1.2 eq) in THF (3 mL) at −78° C. After one hour, tributyltin chloride (165 μL, 0.61 mmol, 1.2 eq) was added neat to the mixture. After 5 min at −78° C., the reaction was quenched with a saturated solution of sodium bicarbonate, and the mixture was warmed to room temperature. The mixture was extracted using methylene chloride (2×10 mL). The combined organic layers were dried over sodium sulfate and filtered. The solvents were removed by evaporation and the product purified by radial PLC (1% TEA/20% EtOAc/hexanes) to afford 125 mg (51%) of a colorless oil: $[α]^{27}_D$ −81 (c 3.9, CH$_2$Cl$_2$); IR(CDCl$_3$) 2955, 2922, 2871, 2851, 2778, 1556, 1450, 1357, 1108, 1055 cm$^{-1}$; $^1$H NMR (400 MHz, CDCl$_3$) δ 8.42 (s, 1H), 7.29 (s, 1H), 3.24 (dt, J=2.4 Hz, J=9.2 Hz, 1H), 2.97 (t, J=8.4 Hz, 1H), 2.28 (q, J=9.2 Hz, 1H), 2.15-2.06 (m, 1H), 2.13 (s, 1H), 1.98-1.90 (m, 1H), 1.82-1.76 (m, 1H), 1.64-1.56 (m, 1H), 1.51-1.46 (m, 6H), 1.33 (q, J=7.2 Hz, 6H), 1.11-1.07 (m, 6H), 0.89 (t, J=7.2 Hz, 9H); $^{13}$C NMR (100 MHz, CDCl$_3$) δ 157.0, 149.6, 148.5, 144.2, 131.3, 72.0, 57.0, 41.0, 36.8, 29.2, 27.6, 22.6, 13.9, 11.2; HRMS Calcd for C$_{22}$H$_{39}$ClN$_2$Sn [M+H]$^+$: 487.1902, Found 487.1881.

Example 4

(S)-5,6-Dichloro-4-iodonicotine (V)

A solution of n-BuLi (0.713 mmol, 1.1 equiv) in hexanes was added to a solution of (S)-5,6-dichloronicotine (150 mg, 0.65 mmol, 1.0 equiv) in THF (2 mL) at −78° C. After 1 h at −78° C., a solution of iodine (200 mg, 0.78 mmol, 1.2 equiv) was added to the mixture at −78° C. After 5 min at −78° C., the reaction was quenched with a saturated solution of sodium bicarbonate (1 mL) and a saturated solution of sodium thiosulfate (1 mL). The mixture was immediately extracted with methylene chloride (2×10 mL). The combined organic layers were dried over potassium carbonate and filtered. The solvents were removed by evaporation, and the product was purified by radial PLC (1% TEA/10% EtOAc/hexanes) to afford 185 mg (80%) of a white solid, mp 107-108° C.: $[α]^{27}_D$ −158 (c 1.6, CH$_2$Cl$_2$); IR (thin film) 2969, 2944, 2844, 2786, 1539, 1512, 1456, 1397, 1357, 1341, 1183, 1155 cm$^{-1}$; $^1$H NMR (400 MHz, CDCl$_3$) δ 8.28 (s, 1H), 3.43 (t, J=8.4 Hz, 1H), 3.27 (dt, J=2.0, 8.2 Hz, 1H), 2.52-2.35 (m, 2H), 2.24 (s, 3H), 1.94-1.76 (m, 2H), 1.50-1.40 (m, 1H); $^{13}$C NMR (100 MHz, CDCl$_3$) δ 146.8, 146.5, 144.3, 135.2, 117.5, 73.5, 57.0, 40.8, 33.8, 23.0; HRMS calcd for C$_{10}$H$_{11}$Cl$_2$IN$_2$ ([M+H]$^+$) 356.9422, found 356.9420.

Example 5

(S)-6-Chloro-2-iodonicotine (VI)

A solution of 2,2,6,6-tetramethylpiperidine (0.76 mmol, 129 μL, 3.0 equiv) in dry THF (1.0 mL) was treated with n-butyllithium (3.0 equiv) at −78° C. After 1 h at −78° C., a solution of (S)-6-chloronicotine (50 mg, 0.25 mmol, 1.0 equiv) in dry THF (0.5 mL) was added dropwise at −78° C. After 1 h at −78° C., a solution of iodine (70 mg, 0.275 mmol, 1.1 equiv) in dry THF (1.0 mL, dried over 4 Å molecular sieves) was added at −78° C. The resulting mixture was stirred at this temperature for 1 h before being quenched with 1 mL of a saturated aqueous solution of sodium bicarbonate and 1 mL of a saturated aqueous solution of sodium thiosulfate. The aqueous layer was extracted with methylene chloride (2×5 mL). The combined organic layers were dried over potassium carbonate. The solvent was removed by evaporation under reduced pressure to afford a yellow oil. The product was purified by radial PLC (silica gel, 1% TEA/hexanes) to afford 78 mg (97%) of a colorless oil: $[α]^{28.5}_D$ −147 (c 1.5, CH$_2$Cl$_2$); IR (neat) 2967, 2942, 2787, 1563, 1539, 1412, 1310 cm$^{-1}$; $^1$H NMR (400 MHz, CDCl$_3$) δ 7.70 (d, J=8.4 Hz, 1H), 7.27 (d, J=8.4 Hz, 1H), 3.33 (t, J=8.0 Hz, 1H), 3.24 (dt, J=2.4, 8.0 Hz, 1H), 2.46-2.36 (m, 2H), 2.19 (s, 3H), 1.90-1.82 (m, 2H), 1.50-1.38 (m, 1H); $^{13}$C NMR (100 MHz, CDCl$_3$) δ 148.8, 143.4, 138.1, 134.5, 124.2, 71.8, 57.0, 40.6, 33.9, 23.1; HRMS calcd for C$_{10}$H$_{12}$IN$_2$Cl ([M+H]$^+$) 322.9812, found 322.9808.

Examples 6-7

Synthesis and Regioselective Substitution of (S)-5-Chloronicotine

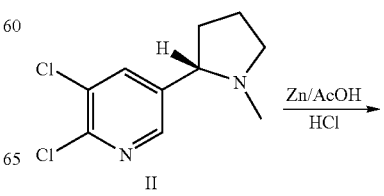

II

-continued

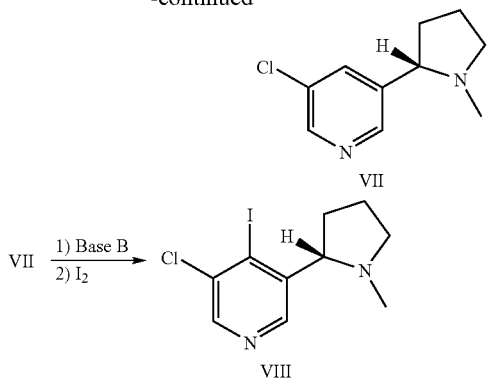

Base B: n-BuLi

Example 6

(S)-5-Chloronicotine (VII)

To a solution of (S)-5,6-dichloronicotine (74 mg, 0.32 mmol, 1.0 eq) in a 1.0 M solution of hydrochloric acid in acetic acid (2 mL) was added zinc powder (84 mg, 1.28 mmol, 4.0 eq). The suspension was stirred at 60° C. until disappearance of starting material (~2 h, monitored by TLC using a co-spot with a solution of 10% ammonium hydroxide). The reaction was cooled to room, temperature, and the acetic acid was removed under reduced pressure. The residue was dissolved in deionized water and methylene chloride, and solid sodium carbonate was added until pH=10. The mixture was extracted with methylene chloride. The combined organic layers were dried over potassium carbonate, filtered through Celite and silica gel, and the solvents were removed under reduced pressure. The product was purified by radial PLC (1% TEA/50% EtOAc/hexanes) to afford 41 mg (65% yield) of a light yellow oil: $[\alpha]^{31}_D$ –148 (c 0.9, $CH_2Cl_2$); IR (neat) 2968, 2944, 2780, 1581, 1563, 1453, 1418, 1354, 1292, 1214, 1100, 1044, 1022, 882, 709 cm$^{-1}$; $^1$H NMR (400 Hz, $CDCl_3$) δ 8.44 (d, J=2.4 Hz, 1H), 8.40 (d, J=1.6 Hz, 1H), 7.71 (dd, J=2.4 Hz, J=1.6 Hz, 1H), 3.23 (dt, J=2.4, 8.4 Hz, 1H), 3.11 (t, J=8.0 Hz, 1H), 2.32 (q, J=8.4 Hz, 1H), 2.26-2.18 (m, 1H), 2.18 (s, 3H), 2.01-1.8 (m, 1H), 1.88-1.76 (m, 1H), 1.7-1.64 (m, 1H); $^{13}$C NMR (100 MHz, $CDCl_3$) δ 147.7, 147.5, 141.0, 134.7, 132.5, 68.3, 57.1, 40.6, 35.6, 22.9; HRMS calcd for $C_{10}H_{13}ClN_2$ ([M+H]$^+$) 197.0846, found 197.0853.

Example 7

(S)-5-Chloro-4-iodonicotine (VIII)

A solution of (S)-5-chloronicotine (50 mg, 0.251 mmol, 1.0 equiv) in THF (1.0 mL) was added to a solution of n-BuLi (0.28 mmol, 1.1 equiv) in THF (1.0 mL) at –78° C. After 1 h at –78° C., a solution of iodine (77 mg, 0.302 mmol, 1.2 equiv) in THF (1 mL) was added to the mixture at –78° C. The reaction was quenched after 5 min at –78° C. with a saturated aqueous solution of sodium bicarbonate (1 mL) and a saturated aqueous solution of sodium thiosulfate (1 mL). The mixture was warmed up and the mixture was extracted with methylene chloride (3×2 mL). The combined organic layers were dried over potassium carbonate, filtered through Celite and silica gel, and concentrated under reduced pressure. The product was purified by radial PLC (1% TEA/20% EtOAc/hexanes) to afford 29 mg (65%) of a white solid, mp 136-137° C.: $[\alpha]^{30}_D$ –150 (c 1.5, $CH_2Cl_2$); IR (neat) 2972, 2941, 2832, 2807, 1392, 1219, 1149, 1051 cm$^{-1}$; $^1$H NMR (400 MHz, $CDCl_3$) δ 8.44 (s, 1H), 8.41 (s, 1H), 3.48 (t, J=8.4 Hz, 1H), 3.28 (m, 1H), 2.51-2.34 (m, 2H), 2.25 (s, 3H), 1.98-1.78 (m, 2H), 1.54-1.42 (m, 1H); $^{13}$C NMR (100 MHz, $CDCl_3$) δ 146.9, 146.8, 144.8, 137.3, 115.5, 73.5, 57.1, 40.8, 33.8, 23.0; HRMS calcd for $C_{10}H_{12}ClN_2$ [M+H]$^+$ 322.9812, found 322.9801.

Examples 8-10

Synthesis and Regioselective Substitution of (S)-6-Methoxynicotine

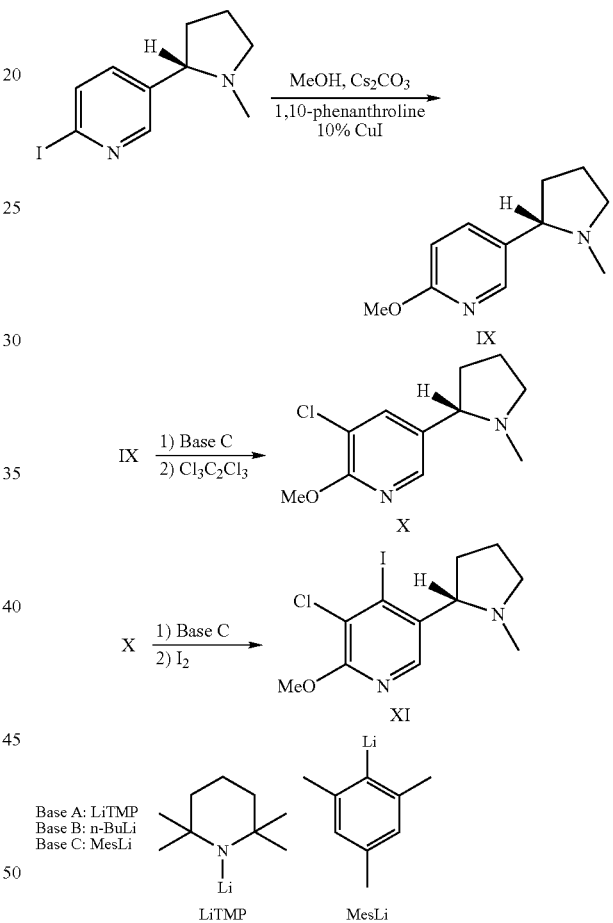

Base A: LiTMP
Base B: n-BuLi
Base C: MesLi

Example 8

(S)-6-Methoxynicotine (IX)

A 15 mL pressure vessel was charged with CuI (99.5 mg, 0.52 mmol, 0.1 eq), 1,10-phenanthroline (190 mg, 1.05 mmol, 0.2 eq), $Cs_2CO_3$ (3.4 g, 10.45 mmol, 2.0 eq) and a solution of (S)-6-iodonicotine (1.51 g, 5.23 mmol, 1.0 eq) in 5 mL of methanol. The tube was sealed and the reaction mixture was stirred at 110° C. for 20 h. The resulting mixture was cooled to room temperature and filtered through a plug of Celite with ethyl acetate. The filtrate was concentrated under reduced pressure. Purification of the residual by radial PLC (1% TEA/20% EtOAc/hexanes) afforded 870 mg (87%) of a clear oil: $[\alpha]^{31}_D$ –139 (c 0.98, $CH_2Cl_2$); IR (neat) 2968, 2945, 2775, 1608, 1495, 1282, 1029, 831 $cm^{-1}$; $^1H$ NMR (400 MHz, $CDCl_3$) δ 8.01 (d, J=2.4 Hz, 1H), 7.6 (dd, J=8.4, 2.4 Hz, 1H), 6.71 (d, 8.4 Hz, 1H), 3.91 (s, 3H), 3.20 (td, J=11.2, 2.4 Hz, 1H), 2.97 (t, J=11 Hz, 1H), 2.25 (q, J=8.4 Hz 1H), 2.17-2.14 (m, 1H), 2.13 (s, 3H), 1.88-1.98 (m, 1H), 1.74-1.82 (m, 1H), 1.64-1.71 (m, 1H); $^{13}C$ NMR (100 MHz, $CDCl_3$) δ 22.6, 34.9, 40.4, 53.5, 57.1, 68.5, 111.2, 131.3, 137.9, 146.2, 163.9; HRMS calcd for $C_{11}H_{16}N_2O$ [M+H]$^+$ 193.1341, found 193.1347.

Example 9

(S)-5-Chloro-6-methoxynicotine (X)

To a solution of t-BuLi (7.33 mL (1.7 M in pentane), 10.83 mmol, 4.0 eq) in freshly distilled THF (5 mL) at –78° C. was added dropwise bromomesitylene (830 μL, 5.41 mmol, 2.0 eq). After stirring the mixture at –78° C. for 1 h, (S)-6-methoxynicotine (500 μL, 2.71 mmol, 1.0 eq) was added dropwise and the temperature was raised to 0° C. The mixture was stirred at 0° C. for 2 h and then cooled to –78° C. A solution of hexachloroethane (1.41 g, 5.95 mmol) in THF (2 mL) was added to the mixture. After 20 min at –78° C., the reaction was quenched with 5 mL of a saturated aqueous solution of sodium bicarbonate. The mixture was extracted with methylene chloride (2×10 mL). The combined organic layers were dried over potassium carbonate and filtered through Celite. The solvent was removed under reduced pressure to afford a light yellow oil. The crude product was purified by radial PLC (1% TEA/2% EtOAc/hexanes) to afford 536 mg (88%) of a clear oil: $[\alpha]_D^{31}$ –148 (c 1.4, $CH_2Cl_2$); IR (neat) 2971, 2777, 1598, 1477, 1402, 1348, 1070, 1018 $cm^{-1}$; $^1H$ NMR (400 MHz, $CDCl_3$) δ 7.90 (d, J=1.6 Hz, 1H), 7.67 (d, J=1.6 Hz, 1H), 3.98 (s, 3H), 3.19 (td, J=8.6, 2.0 Hz, 1H), 2.99 (t, J=8 Hz, 1H), 2.25 (q, J=9.0 Hz, 1H), 2.17-2.14 (m, 1H), 2.12 (s, 3H), 1.86-1.96 (m, 1H), 1.74-1.82 (m, 1H), 1.62-1.71 (m, 1H); $^{13}C$ NMR (100 MHz, $CDCl_3$) δ 22.7, 35.2, 40.5; 54.5, 57.0, 57.1, 67.1, 67.9, 118.7, 133.1, 137.5, 143.8, 159.0; HRMS calcd for $C_{11}H_{15}ClN_2O$ [M+H]$^+$ 227.0951, found 227.0954.

Example 10

(S)-5-Chloro-4-iodo-6-methoxynicotine (XI)

A solution of (S)-5-chloro-6-methoxynicotine (50.0 mg, 0.22 mmol, 1.0 eq) in dry THF (2 mL) at –78° C. was treated dropwise with n-BuLi (130 μL (2.5 M in hexanes), 0.27 mmol, 1.2 eq). After 1 h at –78° C., a solution of iodine (67.4 mg, 0.27 mmol, 1.2 eq) in THF (1 mL) was added, and the mixture was stirred for an additional 10 min. The reaction was quenched with 3 mL of a saturated aqueous solution of sodium bicarbonate. The product was extracted with methylene chloride (2×10 mL) The combined organic extracts were washed with 3 mL of a saturated solution of sodium thiosulfate, dried over potassium carbonate, and filtered through Celite. The solvent was removed under reduced pressure to give a residue that was purified by radial PLC (2% MeOH/$CH_2Cl_2$) to afford 64.9 mg (83%) of a white solid, mp 87-94° C.: $[\alpha]_D^{30}$ –122 (c 1.0, $CH_2Cl_2$); IR(neat) 2942, 2787, 1564, 1464, 1369, 1025 $cm^{-1}$; $^1H$ NMR (400 MHz, $CDCl_3$) δ 8.07 (s, 1H), 4.01 (s, 3H), 3.37 (t, J=8.0 Hz, 1H), 3.24 (td, J=8.0, 1.8 Hz, 1H), 2.39-2.45 (m, 1H), 2.34 (q, J=8.4 Hz, 1H), 2.23 (s, 3H), 1.74-1.92 (m, 2H), 1.4-1.5 (m, 1H); $^{13}C$ NMR (100 MHz, $CDCl_3$) δ 22.8, 34.1, 40.8, 54.9, 57.0, 73.1, 117.5, 123.0, 136.8, 143.7, 158.6.

Examples 11-14

Preparation of (S)-4-Aryl(heteroaryl)nicotine Derivatives

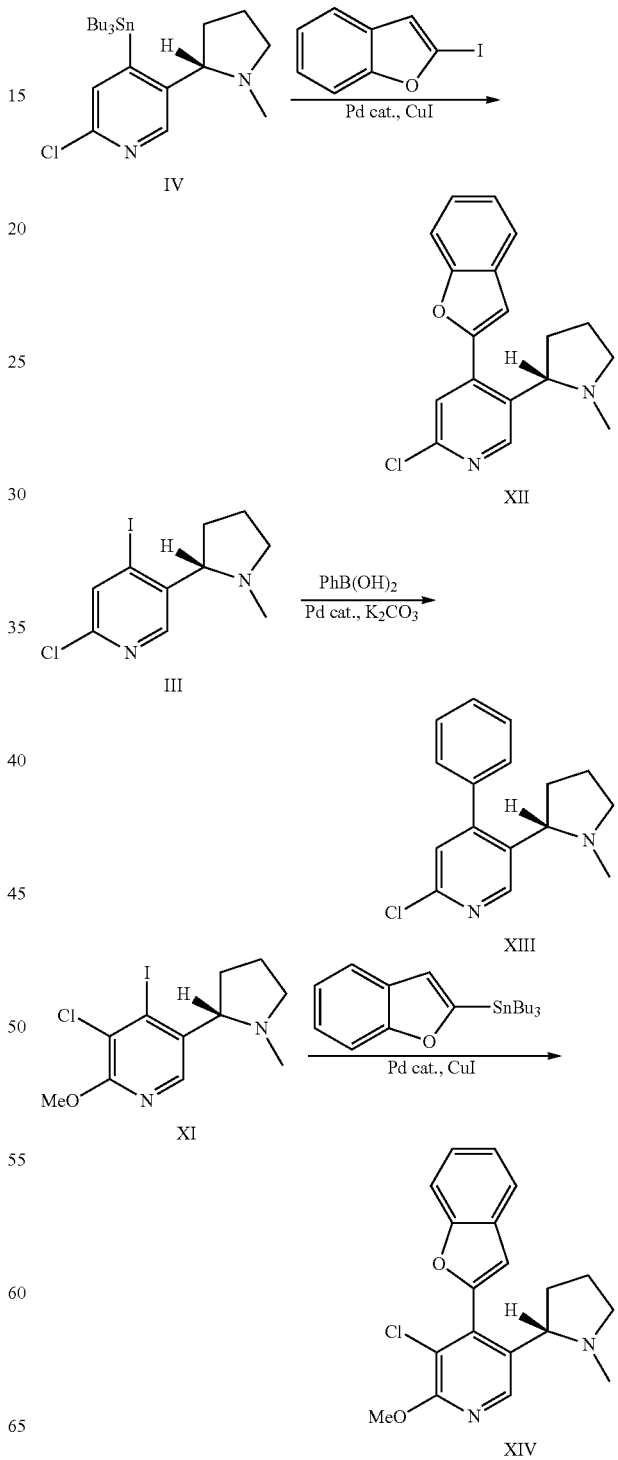

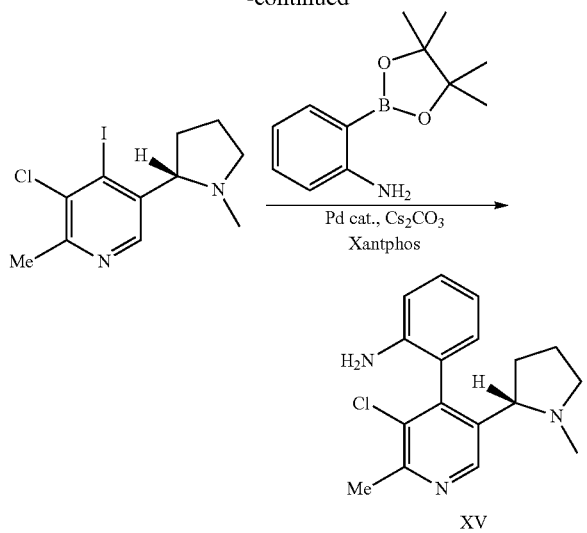

Example 11

(S)-4-Benzofuran-6-chloronicotine (XII)

A solution of (S)-6-chloro-4-(tributylstannyl)nicotine (217 mg, 0.45 mol, 1.0 eq), 2-iodobenzofuran (131 mg; 0.54 mmol, 1.2 eq), Pd(PPh$_3$)$_4$ (52 mg, 0.04 mmol, 10%), CuI (17 mg, 0.09 mmol, 20%) in toluene (3 mL) was degassed for 20 minutes with nitrogen. The mixture was then heated to 80° C. and stirred at that temperature for 44 h. The reaction was allowed to cool to room temperature, and then 2 mL of a solution of a 1:1 mixture of ammonium hydroxide and ammonium chloride was added. The mixture was extracted with methylene chloride (2×10 mL), The combined organic extracts were dried over potassium carbonate and filtered through Celite. The solvent was removed under reduced pressure. The residue was purified by column chromatography on basic alumina (1% TEA/2% EtOAc/hexanes) to afford 71.5 mg (51%) of a white solid, mp 103-110° C.: [α]$_D^{29}$ −148 (c 0.9, CH$_2$Cl$_2$); IR 2975, 2952, 2846, 2785, 1584, 1446, 1097, 872, 748 cm$^{-1}$; $^1$H NMR (400 MHz, CDCl$_3$) δ 8.86 (d, J=0.8 Hz, 1H), 7.68 (dd, J=7.2, 1.2 Hz, 2H), 7.59 (dd, J=8.8, 0.8 Hz, 1H), 7.40 (td, J=7.6, 1.2 Hz, 1H), 7.31 (d, J=8.8, 0.8 Hz, 1H), 7.10 (d, J=0.8 Hz, 1H) 3.71 (t, J=8.4 Hz, 1H), 3.27 (t, J=8.4 Hz, 1H), 2.40-2.48 (m, 1H), 2.35 (q, J=9.2 Hz, 1H), 2.20 (s, 3H), 1.95-2.05 (m, 1H), 1.80-1.90 (m, 1H), 1.70-1.80 (m, 1H); $^{13}$C NMR (100 MHz, CDCl$_3$) δ 23.4, 35.3, 40.8, 57.1, 65.4, 108.9, 111.7, 121.8, 121.9, 123.7, 126.0, 128.5, 135.5, 139.7, 150.0 151.1, 151.4, 155.3; HRMS calcd for C$_{18}$H$_{17}$ClN$_2$O [M+H]$^+$ 313.1108, found 313.1118.

Example 12

(S)-6-Chloro-4-phenylnicotine (XIII)

A solution of (S)-6-chloro-4-iodonicotine (50 mg, 0.16 mol, 1.0 eq), phenylboronic acid (28 mg, 0.23 mmol, 1.5 eq), Pd(PPh$_3$)$_4$ (18 mg, 0.02 mmol, 10%) and potassium carbonate (43 mg, 0.31 mmol, 2.0 eq) in toluene (3 mL) was degassed for 15 minutes with nitrogen. The mixture was heated at reflux for 3 d. The reaction was allowed to cool to room temperature, 1 mL of water added, and the mixture was extracted with methylene chloride (2×10 mL). The combined organic extracts were dried over sodium sulfate and filtered through Celite. The solvent was removed under reduced pressure. The crude product was purified by radial PLC (1% TEA/20% EtOAc/hexanes) to afford 24 mg (56%) of a pale yellow oil: [α]$_D^{30}$ −151 (c 1.5, CH$_2$Cl$_2$); IR (neat) 2971, 2945, 2838, 2785, 1580, 1455, 1097, 1044 cm$^{-1}$; $^1$H NMR (400 MHz, CDCl$_3$) δ 8.67 (s, 1H), 7.43-7.4 (m, 3H), 7.19-7.2 (m, 2H), 7.11 (s, 1H), 3.04-3.22 (m, 2H), 2.01-2.18 (m, 2H), 2.06 (s, 3H), 1.84-1.92 (m, 1H), 1.60-1.72 (m, 2H); $^{13}$C NMR (100 MHz, CDCl$_3$) δ 22.9, 35.8, 40.4, 56.8, 64.9, 124, 128.4 (2C), 128.5 (3C), 136, 137.6, 149.1, 150.2, 152.7; HRMS calcd for C$_{16}$H$_{17}$ClN$_2$ [M+H]$^+$ 273.1159, found 273.1147.

Example 13

(S)-4-Benzofuran-5-chloro-6-methoxynicotine (XIV)

A solution of (S)-5-chloro-4-iodo-6-methoxynicotine (40 mg, 0.11 mol, 1.0 eq), 2-(tributylstannyl)benzofuran (55 mg, 0.14 mmol, 1.2 eq), Pd(PPh$_3$)$_4$ (131 mg, 0.01 mmol, 10%) and CuI (4 mg, 0.02 mmol, 20%) in toluene (3 mL) was placed in a 15-mL pressure vessel and degassed for 20 minutes with nitrogen. The tube was sealed and the reaction mixture stirred at 95° C. for 2 days. The mixture was allowed to cool to room temperature and 2 mL of a solution of a 1:1 mixture of ammonium hydroxide and ammonium chloride was added. The mixture was extracted with methylene chloride (2×10 mL). The combined organic layers were dried over potassium carbonate and filtered through Celite. The crude product was purified by radial PLC (1% TEA/10% EtOAc/hexanes) to afford 30 mg (77%) of a clear oil: [α]$_D^{31}$ −109 (c 1.5, CH$_2$Cl$_2$); IR (neat) 2946, 2839, 2780, 1573, 1469, 1453, 1385, 1294, 1092, 1023, 748 cm$^{-1}$; $^1$H NMR (400 MHz, CDCl$_3$) δ 8.45 (s, 1H), 7.67 (dt, J=7.6, 0.8 Hz, 1H), 7.55 (d, J=8 Hz, 1H), 7.36 (td, J=7.6, 1.6 Hz, 1H), 7.31 (td, J=7.6, 0.8 Hz, 1H), 6.88 (s, 1H), 4.08 (s, 3H), 3.14 (td, J=8.0, 1.2 Hz, 1H), 3.00 (t, J=8.0 Hz, 1H), 2.15 (s, 3H), 2.09-2.11 (m, 2H), 1.84-1.93 (m, 1H), 1.62-1.75 (m, 2H); $^{13}$C NMR (100 MHz, CDCl$_3$) δ 22.9, 35.9, 40.6, 54.7, 56.9, 66.2, 108.8, 111.7, 117.7, 121.6, 123.4, 125.0, 128.3, 133.7, 139.5, 144.3, 149.4, 155.1, 158.7.

Example 14

(S)-5-Chloro-6-methyl-4-(2-phenylamino)nicotine (XV)

A solution of (S)-5-chloro-6-methyl-4-iodonicotine (100 mg, 0.297 mmol, 1.0 equiv), Pd$_2$dba$_3$ (14 mg, 0.015 mmol, 5%), cesium carbonate (145 mg, 0.445 mmol, 1.5 equiv), 2-(pinacolborane)aniline (65 mg, 0.297 mmol, 1.0 equiv) and Xantphos (18 mg, 0.030 mmol, 10%) in 1,4-dioxane (4 mL) was placed in a pressure tube and degassed with argon for 15 min. The mixture was warmed to 110° C. and stirred for 14 h. The reaction was cooled to room temperature and poured into deionized water (5 mL). The mixture was extracted with methylene chloride (3×3 mL). The combined organic layers were dried over potassium carbonate, filtered and concentrated. The product was purified by radial PLC (1% TEA/75% EtOAc/hexanes) to afford 69 mg (77%) of an off-white foam: [α]$^{30}{}_D$ −117 (c 1.9, CH$_2$Cl$_2$); IR (neat) 3464, 3338, 3218, 2971, 2944, 2844, 2784, 1652, 1632, 1615, 1582, 1506, 1498, 1452, 1382, 1305, 1182, 1082, 908, 748, 735 cm$^{-1}$; $^1$H NMR (400 Hz, CDCl$_3$) δ 8.72 and 8.69 (rotomers, s, 1H), 7.26-7.21 (m, 1H), 6.86-6.82 (m, 2H), 6.78 (dd, J=1.2, 8.4 Hz, 1H), 3.39 (bs, 2H), 3.13 (t, J=7.6 Hz, 1H), 2.96 (t, J=8.0 Hz, 1H), 2.68 (s, 3H), 2.16-2.06 (m, 1H), 2.13 (s, 3H), 2.06-1.96 (m, 1H), 1.90-1.76 (m, 1H), 1.68-1.54 (m, 2H); $^{13}$C NMR (100 MHz, CDCl$_3$) δ 154.9, 147.2, 146.7 (due to rotomers), 145.4, 144.0, 142.7, 138.2 (due to rotomers), 137.9, 131.1, 129.9 (due to rotomers), 129.8 (due to rotomers), 129.7, 129.2, 121.8, 121.8 (due to rotomers), 118.7, 118.5 (due to rotomers), 115.8, 115.6 (due to rotomers), 66.6 (due to rotomers), 66.0, 57.0, 56.8 (due to rotomers), 40.8, 40.6, 35.4 (due to rotomers), 35.1, 23.5, 22.8, 22.7 (due to rotomers); HRMS calcd for C$_{17}$H$_{20}$ClN$_3$ ([M+H]$^+$) 302.1424, found 302.1429.

Examples 15-16

Preparation of (S)-6-Amino or 6-Alkyl(aryl)nicotine Derivatives

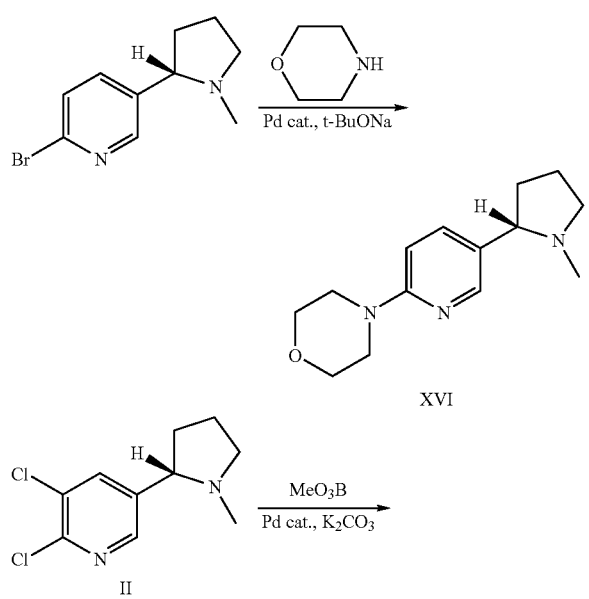

Example 15

(S)-6-Morpholinonicotine (XVI)

A mixture of (S)-6-bromonicotine (287 mg, 1.2 mmol), morpholine (125 pt, 1.4 mmol, 1.2 eq), sodium tert-butoxide (160 mg, 1.7 mmol, 1.4 eq), Pd$_2$(dba)$_3$ (65 mg, 0.07 mmol, 6%), 1,3-bis(diphenylphosphino)propane (dppp, 59 mg, 0.4 mmol, 12%) and toluene (5 mL) was placed in a dry flask and purged with nitrogen for 20 minutes. The reaction mixture was then heated to 80° C. After 24 h, the reaction mixture was allowed to cool to room temperature and was washed with 2 mL of water. The mixture was extracted with methylene chloride (2×10 mL). The combined organic layers were dried over MgSO$_4$ and filtered through a plug of Celite and silica. The solvent was removed under reduced pressure to give the crude product. Purification by radial PLC (1% TEA/10% EtOAc/hexanes) afforded 195 mg (66%) of a pale yellow oil.

[α]$_D^{29}$ –128 (c 1.64, CH$_2$Cl$_2$); $^1$H NMR (400 MHz, CDCl$_3$) δ 8.0 (d, J=2 Hz, 1H), 7.46 (dd, J=8.6, 2.0 Hz, 1H), 6.56 (d, J=8.4 Hz, 1H), 3.72 (t, J=–5.2 Hz, 4H) 3.39 (t, J=5.2 Hz, 4H), 3.11 (td, J=9.0, 2.0 Hz, 1H), 2.85 (t, J=8.8 Hz, 1H), 2.13 (q, J=8.8 Hz, 1H), 2.04 (s, 3H), 2.03-1.95 (m, 1H), 1.8-1.9 (m, 1H), 1.55-1.7 (m, 2H); $^{13}$C NMR (100 MHz, CDCl$_3$) δ 22.2, 34.5, 40.2, 45.7, 56.8, 66.7, 68.4, 107.2, 127.8, 136.6, 147.4, 159.2; IR 2995, 2850, 2781, 1603, 1496, 1447, 1249, 1120, 945 cm$^{-1}$. HRMS calcd for C$_{14}$H$_{21}$N$_3$O (MH$^+$) 248.1763, found 248.1776.

Example 16

(S)-5-Chloro-6-methylnicotine (XVII)

A solution of (S)-5,6-dichloronicotine (800 mg, 3.461 mmol), potassium carbonate (718 mg, 5.192 mmol, 1.5 equiv), Pd(PPh$_3$)$_4$ (400 mg, 0.346 mmol, 0.1 equiv) and trimethylboroxine (480 µL, 3.461 mmol, 1.0 equiv) in 1,4-dioxane (5 mL) was degassed with argon for 15 min, then stirred at 110° C. for 3 d. The mixture was cooled to room temperature, poured into deionized water (4 mL), and extracted with CH$_2$Cl$_2$ (3×3 mL). The combined organic layers were dried over K$_2$CO$_3$, filtered through a pad of Celite, and silica and concentrated. The product was purified by radial PLC (1% TEA/50% EtOAc/hexanes) to afford 512 mg of a light-yellow oil (70%). [α]$_D^{29}$ –155 (c 0.75, CH$_2$Cl$_2$); IR (neat): 2969, 2946, 2840, 2779, 1594, 1460, 1396, 1335, 1216, 1056, 902, 722 cm$^{-1}$; $^1$H NMR (300 MHz, CDCl$_3$) δ 8.28 (d, J=2.1 Hz, 1H), 7.66 (d, J=2.1 Hz, 1H), 3.23 (t, J=8.25 Hz, 1H), 3.06 (t, J=8.1 Hz, 1H), 2.60 (s, 3H), 2.30 (q, J=8.4 Hz, 1H), 2.21-2.17 (m, 1H), 2.17 (s, 3H), 2.00-1.90 (m, 1H), 1.90-1.80 (m, 1H), 1.80-1.65 (m, 1H); $^{13}$C NMR (100 MHz, CDCl$_3$) δ 155.0, 146.8, 138.5, 135.5, 131.8, 68.2, 57.2, 40.6, 35.5, 22.8, 22.6; HRMS calcd for C$_{11}$H$_{15}$ClN$_2$ ([M+H]$^+$) 211.1002, found 211.1004.

Example 17

(S)-Brevicolline (XVIII)

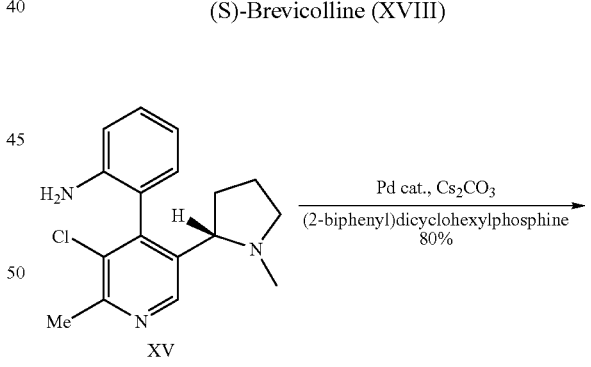

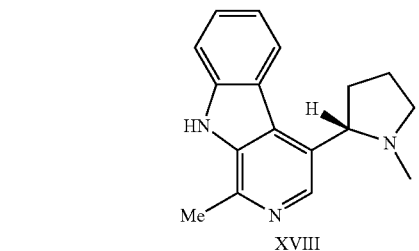

A solution of (S)-5-chloro-6-methyl-4-[(2-amino)phenyl]nicotine (25 mg, 0.082 mmol), Pd$_2$dba$_3$ (8 mg, 0.008 mmol, 0.1 equiv), (2-biphenyl)dicyclohexylphosphine (6 mg, 0.016 mmol, 0.2 equiv) and cesium carbonate (40 mg, 0.124 mmol, 1.5 equiv) in dioxane (2 mL) was degassed with argon for 15 min and then warmed to 100° C. for 23 h. The reaction mixture was cooled to room temperature and poured into a saturated aqueous solution, of sodium bicarbonate. The product was extracted with methylene chloride (3×3 mL). The combined organic layers were dried over potassium carbonate, filtered through Celite, and concentrated. The product was purified by radial PLC (10% MeOH/CH$_2$Cl$_2$) to afford 18 mg (80%) of a white solid, mp 228-229° C. [α]$^{31}_D$ −165 (c 0.62, EtOH); $^1$H NMR (400 MHz, CDCl$_3$) δ 9.04 (bs, 1H), 8.49 (s, 1H), 8.45 (d, J=8.0 Hz, 1H), 7.56-7.48 (m 1H), 7.53 (s, 1H), 7.31-7.25 (m, 1H), 3.91 (t, J=8.0 Hz, 1H), 3.39 (t, J=8.0 Hz, 1H), 2.83 (s, 3H), 2.50-2.40 (m, 2H), 2.30 (s, 3H), 2.14-2.02 (m, 1H), 2.00-1.50 (m, 2H); $^{13}$C NMR (100 MHz, CDCl$_3$) δ 140.5, 137.2, 134.8, 131.4, 127.8, 126.7, 125.8, 122.2, 120.2, 111.7, 104.3, 68.0, 57.4, 41.1, 33.3, 22.9, 20.3.

Note: This is a known compound: Mahboobi, S.; Wiegrebe, W.; Popp, A. *J. Nat. Prod.* 1999, 62, 577, and references cited therein.

The foregoing is illustrative of the present invention, and is not to be construed as limiting thereof. The invention is defined by the following claims, with equivalents of the claims to be included therein.

That which is claimed is:

1. A compound of Formula A:

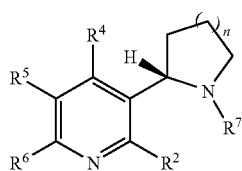

(A)

wherein:
n is 1;
R$^2$ is selected from the group consisting of H, alkyl, aryl, alkoxy and halo;
R$^4$ and R$^5$ are each independently selected from the group consisting of H, alkyl, aryl, heteroaryl, alkenyl, alkynyl, alkoxy, aryloxy, halo, SiR$^{20}$R$^{21}$R$^{22}$, and SnR$^{20}$R$^{21}$R$^{22}$, wherein R$^{20}$, R$^{21}$ and R$^{22}$ are each independently alkyl, aryl, halo, hydroxy or alkoxy; and
R$^6$ is independently selected from the group consisting of H, C$_2$-C$_{12}$ alkyl, aryl, heteroaryl, alkenyl, alkynyl, alkoxy, aryloxy, halo, SiR$^{20}$R$^{21}$R$^{22}$, and SnR$^{20}$R$^{21}$R$^{22}$, wherein R$^{20}$, R$^{21}$ and R$^{22}$ are each independently alkyl, aryl, halo, hydroxy or alkoxy; and
R$^7$ is H or alkyl;
subject to the proviso that either R$^4$ and R$^5$, or R$^5$ and R$^6$, together form a fused ring, wherein:
when R$^5$ and R$^6$ together form a fused ring, said fused ring is selected from the group consisting of:

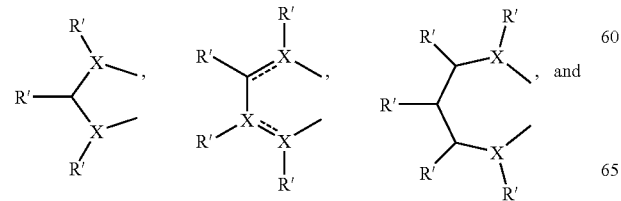

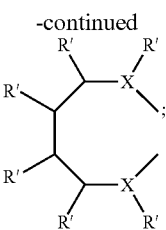

wherein each X is independently selected from the group consisting of C(R'), N, O, SiR', and S; and when R$^5$ and R$^6$ together form a six-membered ring, at least one X is independently selected from the group consisting of N, O, SiR', and S; and each R' is independently selected from the group consisting of H, alkyl, aryl, heteroaryl, alkenyl, alkynyl, alkoxy, aryloxy, and halo; or wherein an adjacent pair of R's together form a fused ring selected from the group consisting of:

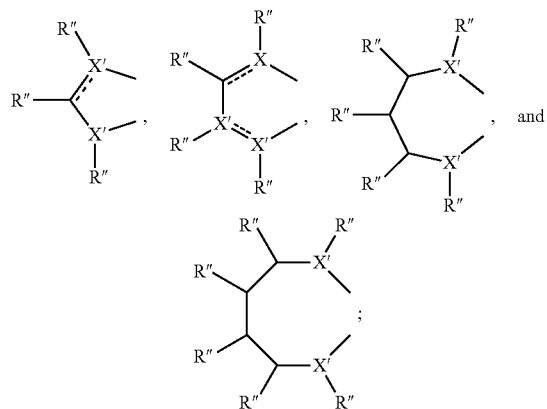

wherein each X' is independently selected from the group consisting of C(R"), N, O, SiR", and S; and
each R" is independently selected from the group consisting of H, alkyl, aryl, heteroaryl, alkenyl, alkynyl, alkoxy, aryloxy, halo;
and
when R$^4$ and R$^5$ together form a fused ring, said fused ring is selected from the group consisting of:

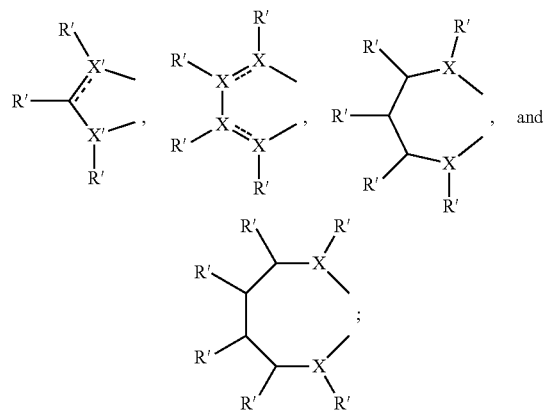

wherein each X is independently selected from the group consisting of C(R'), N, O, SiR', and S; and wherein each R' is independently selected from the group consisting of H, alkyl, aryl, heteroaryl, alkenyl, alkynyl, alkoxy, aryloxy, and halo; or wherein an adjacent pair of R's together form a fused ring selected from the group consisting of:

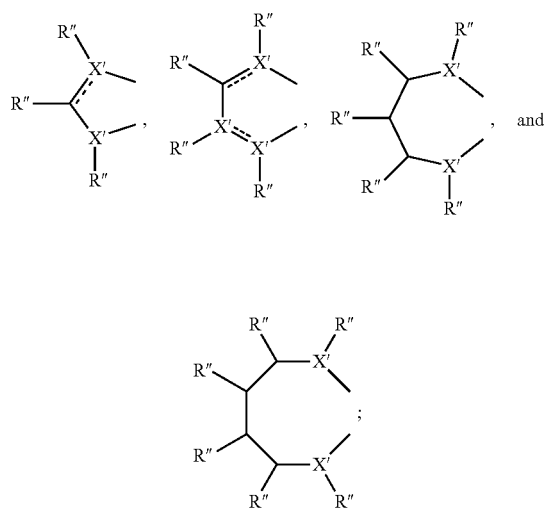

wherein each X' is independently selected from the group consisting of C(R"), N, O, SiR", and S; and each R" is independently selected from the group consisting of H, alkyl, aryl, heteroaryl, alkenyl, alkynyl, alkoxy, aryloxy, and halo;

wherein said heteroaryl is selected from the group consisting of: benzofuranyl, benzo[b]thiophenyl, indolyl, indolyl amine, benzoxazolyl, benzoimidazolyl, benzothiazolyl, isoquinolinyl, quinazolinyl, pyridinyl, furanyl, oxazolyl, isoxazolyl, thiazolyl, and imidazolyl;

or a pharmaceutically acceptable salt or prodrug thereof.

2. The compound of claim 1, wherein $R^4$ and $R^5$ together form a fused ring.

3. The compound of claim 1, wherein $R^5$ and $R^6$ together form a fused ring.

4. A composition comprising a compound of claim 1 in a pharmaceutically acceptable carrier.

5. A compound of Formula A:

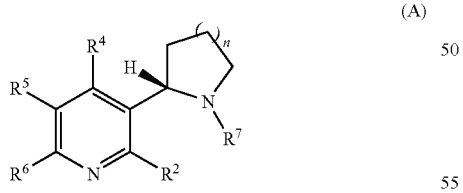

(A)

wherein:

n is 1;

$R^2$ is selected from the group consisting of H, alkyl, and halo;

$R^4$ and $R^5$ are each independently selected from the group consisting of H, alkyl, aryl, heteroaryl, alkenyl, alkynyl, alkoxy, aryloxy, halo, $SiR^{20}R^{21}R^{22}$, and $SnR^{20}R^{21}R^{22}$, wherein $R^{20}$, $R^{21}$ and $R^{22}$ are each independently alkyl, aryl, halo, hydroxy or alkoxy; and $R^6$ is independently selected from the group consisting of H, $C_2$-$C_{12}$ alkyl, aryl, heteroaryl, alkenyl, alkynyl, alkoxy, aryloxy, halo, $SiR^{20}R^{21}R^{22}$, and $SnR^{20}R^{21}R^{22}$, wherein $R^{20}$, $R^{21}$ and $R^{22}$ are each independently alkyl, aryl, halo, hydroxy or alkoxy; and $R^7$ is H or alkyl;

subject to the proviso that either $R^4$ and $R^5$, or $R^5$ and $R^6$, together form a fused ring, wherein:

when $R^5$ and $R^6$ together form a fused ring, said fused ring is selected from the group consisting of:

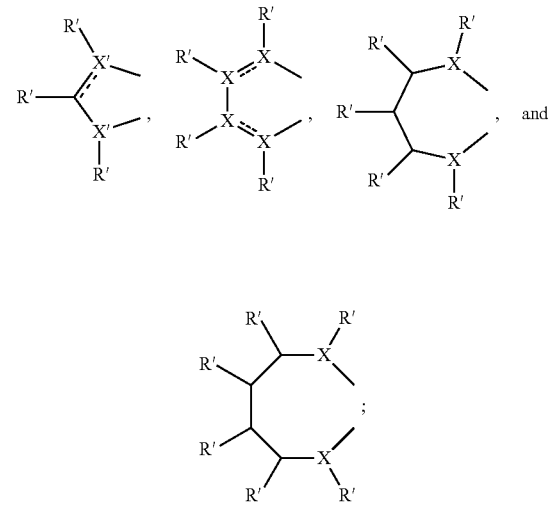

wherein each X is independently selected from the group consisting of C(R'), N, O, SiR', and S; and when $R^5$ and $R^6$ form a six membered ring at least one X is independently selected from the group consisting of N, O, SiR', and S; and each R' is independently selected from the group consisting of H, alkyl, aryl, heteroaryl, alkenyl, alkynyl, alkoxy, aryloxy, and halo: or wherein an adjacent pair of R's to together form a fused ring selected from the group consisting of:

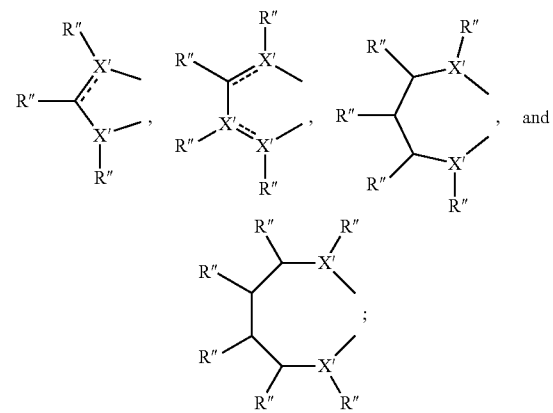

wherein each X' is independently selected from the group consisting of C(R"), N, O, SiR", and S; and each R" is independently selected from the group consisting of H, alkyl, aryl, heteroaryl, alkenyl, alkynyl, alkoxy, aryloxy, halo;

and when $R^4$ and $R^5$ together form a fused ring, said fused ring is selected from the group consisting of:

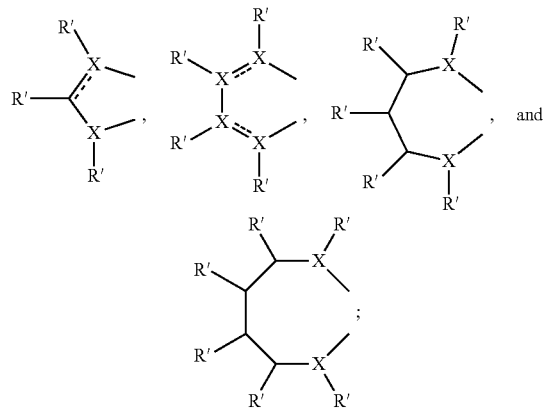

wherein each X is independently selected from the group consisting of C(R'), N, O, SiR', and S; and
wherein each R' is independently selected from the group consisting of H, alkyl, aryl, heteroaryl, alkenyl, alkynyl, alkoxy, aryloxy, and halo; or wherein an adjacent pair of R's together form a fused ring selected from the group consisting of:

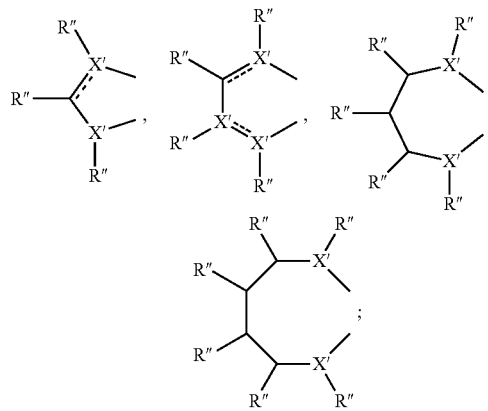

wherein each X' is independently selected from the group consisting of C(R''), N, O, SiR'', and S; and each R'' is independently selected from the group consisting of H, alkyl, aryl, heteroaryl, alkenyl, alkynyl, alkoxy, aryloxy, and halo;
wherein said heteroaryl is selected from the group consisting of: benzofuranyl, benzo[b]thiophenyl, indolyl, indolyl amine, benzoxazolyl, benzoimidazolyl, benzothiazolyl, isoquinolinyl, quinazolinyl, pyridinyl, furanyl, oxazolyl, isoxazolyl, thiazolyl, and imidazolyl;
or a pharmaceutically acceptable salt or prodrug thereof.

6. The compound of claim 5, wherein $R^4$ and $R^5$ together form a fused ring.

7. The compound of claim 5, wherein $R^5$ and $R^6$ together form a fused ring.

8. A composition comprising a compound of claim 5 in a pharmaceutically acceptable carrier.

9. The compound of claim 6, wherein $R^6$ is selected from H, $C_5$-$C_{12}$ alkyl, alkoxy, and halo.

10. The compound of claim 5, wherein said fused ring is a group:

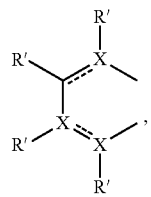

wherein each X and R' are as defined in claim 5.

11. The compound of claim 10, wherein at least one X is independently selected from the group consisting of N and O; and wherein each R' is independently selected from the group consisting of H, alkyl, and halo; or wherein an adjacent pair of R's form an additional fused ring as defined in claim 5.

12. The compound of claim 5, wherein said compound is selected from the group consisting of:

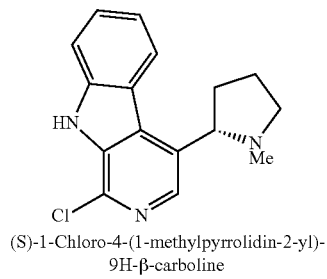

(S)-1-Chloro-4-(1-methylpyrrolidin-2-yl)-9H-β-carboline

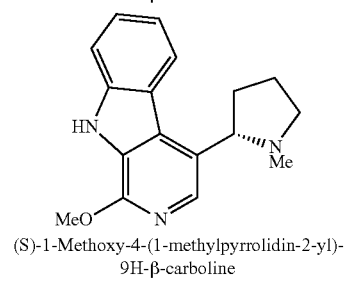

(S)-1-Methoxy-4-(1-methylpyrrolidin-2-yl)-9H-β-carboline

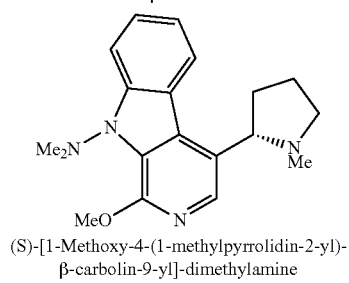

(S)-[1-Methoxy-4-(1-methylpyrrolidin-2-yl)-β-carbolin-9-yl]-dimethylamine

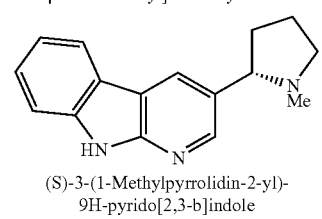

(S)-3-(1-Methylpyrrolidin-2-yl)-9H-pyrido[2,3-b]indole

-continued

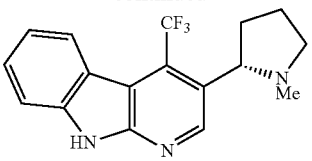
(S)-3-(1-Methylpyrrolidin-2-yl)-4-trifluoromethyl-
9H-pyrido[2,3-b]indole

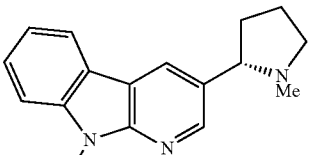
(S)-Dimethyl-[3-(1-methylpyrrolidin-2-yl)-pyrido[2,3-b]indol-9-yl]amine

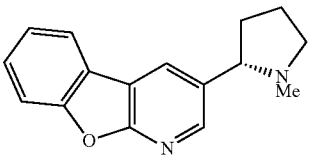
(S)-3-(1-Methylpyrrolidin-2-yl)-
benzo[4,5]furo[2,3-b]pyridine

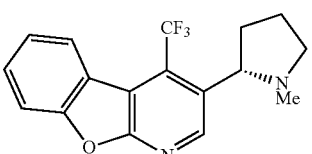
(S)-3-(1-Methylpyrrolidin-2-yl)-4-trifluoromethyl-
benzo[4,5]furo[2,3-b]pyridine

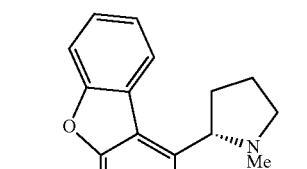
(S)-1-Methoxy-4-(1-methylpyrrolidin-2-yl)-
benzo[4,5]furo[2,3-c]pyridine or a pharmaceutically acceptable salt thereof.

13. The compound of claim 5, wherein said compound is selected from the group consisting of:

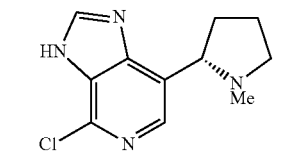
(S)-4-Chloro-7-(1-methylpyrrolidin-2-yl)-
3H-imidazo[4,5-c]pyridine

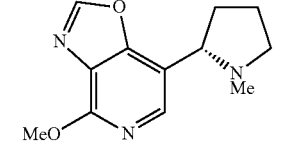
(S)-4-Methoxy-7-(1-methylpyrrolidin-2-yl)-
oxazolo[4,5-c]pyridine

-continued

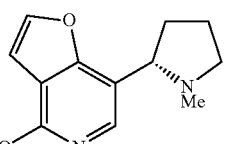
(S)-4-Methoxy-7-(1-methylpyrrolidin-2-yl)-
furo[3,2-c]pyridine

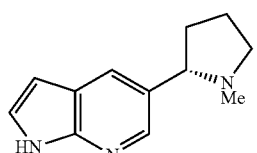
(S)-5-(1-Methylpyrrolidin-2-yl)-
1H-pyrrolo[2,3-b]pyridine

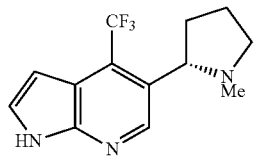
(S)-5-(1-Methylpyrrolidin-2-yl)-4-trifluoromethyl-
1H-pyrrolo[2,3-b]pyridine

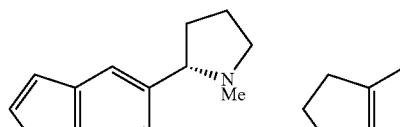 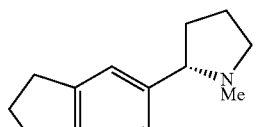

(S)-5-(1-Methylpyrrolidin-2-yl)-
furo[2,3-b]pyridine (S)-5-(1-Methylpyrrolidin-2-yl)-
2,3-dihydrofuro[2,3-b]pyridine

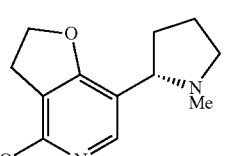
(S)-4-Methoxy-7-(1-methylpyrrolidin-2-yl)-
2,3-dihydrofuro[3,2-c]pyridine

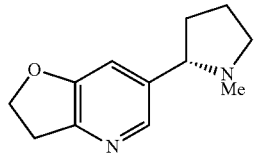
(S)-6-(1-Methylpyrrolidin-2-yl)-2,3-
dihydrofuro[3,2-b]pyridine

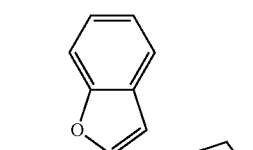
(S)-4-Benzofuran-2-yl-5-(1-methylpyrrolidin-2-yl)-furo[2,3-b]pyridine -continued

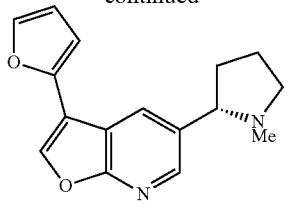

(S)-3-Furan-2-yl-5-(1-methylpyrrolidin-2-yl)-
furo[2,3-b]pyridine

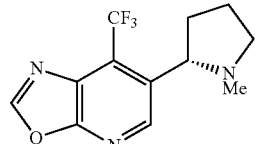

(S)-6-(1-Methylpyrroldin-2-yl)-7-
trifluoromethyloxazolo[5,4-b]pyridine or a pharmaceutically acceptable salt thereof.

14. The compound of claim 5, wherein said compound is selected from the group consisting of:

(S)-5-Chloro-8-(1-methylpyrrolidin-2-yl)-
2,3-dihydro-[1,4]dioxino[2,3-c]pyridine (S)-5-Methoxy-8-(1-methylpyrrolidin-2-yl)-
2,3-dihydro-1H-pyrido[3,4-b][1,4]oxazine (S)-8-(1-Methylpyrrolidin-2-yl)-
1,2,3,4-tetrahydro-pyrido[3,4-b]pyrazine (S)-5-Chloro-8-(1-methylpyrrolidin-2-yl)-
3,4-dihydro-2H-pyrano[3,2-c]pyridine (S)-5-Methoxy-8-(1-methylpyrrolidin-2-yl)-
1,2,3,4-tetrahydro-[1,6]naphthyridine -continued

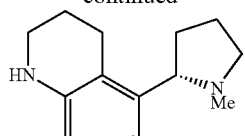

(S)-5-(1-Methylpyrrolidin-2-yl)-1,2,3,4-tetrahydro-[1,7]naphthyridine

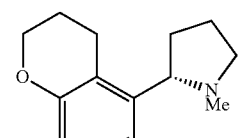

(S)-8-Chloro-5-(1-methylpyrrolidin-2-yl)-
3,4-dihydro-2H-pyrano[2,3-c]pyridine

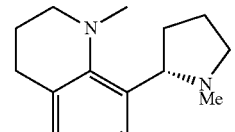

(S)-5-Methoxy-1-methyl-8-(1-methylpyrrolidin-2-yl)-
1,2,3,4-tetrahydro-[1,6]naphthyridine

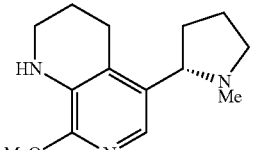

(S)-5-(1-Methylpyrrolidin-2-yl)-
1,2,3,4-tetrahydro-[1,7]naphthyridine or a pharmaceutically acceptable salt thereof.

15. The compound of claim 5, wherein said compound is selected from the group consisting of:

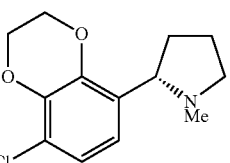 and (S)-5-Chloro-8-(1-methylpyrrolidin-2-yl)-
2,3-dihydro-[1,4]dioxino[2,3-c]pyridine

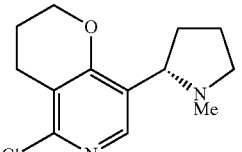, (S)-5-Chloro-8-(1-methylpyrrolidin-2-yl)-
3,4-dihydro-2H-pyrano[3,2-c]pyridine or a pharmaceutically acceptable salt thereof.

16. The compound of claim 5, wherein said compound is selected from the group consisting of:

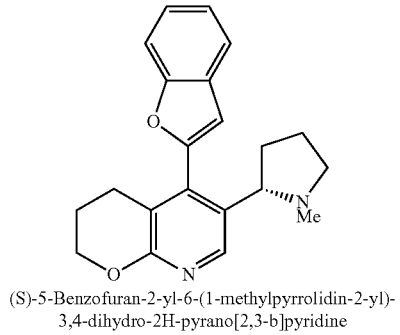

(S)-5-Benzofuran-2-yl-6-(1-methylpyrrolidin-2-yl)-
3,4-dihydro-2H-pyrano[2,3-b]pyridine

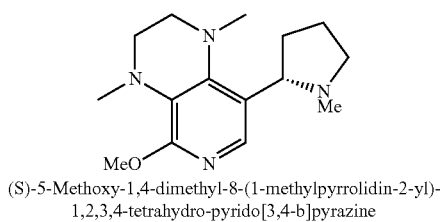

(S)-5-Methoxy-1,4-dimethyl-8-(1-methylpyrrolidin-2-yl)-
1,2,3,4-tetrahydro-pyrido[3,4-b]pyrazine

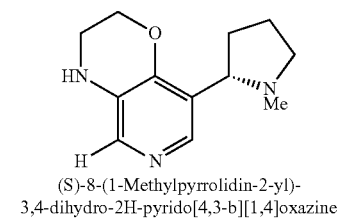

(S)-8-(1-Methylpyrrolidin-2-yl)-
3,4-dihydro-2H-pyrido[4,3-b][1,4]oxazine or a pharmaceutically acceptable salt thereof.

17. The compound of claim 5, wherein said compound is selected from the group consisting of:

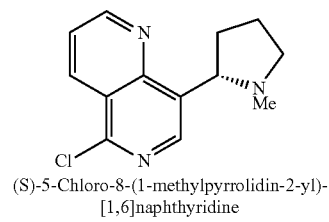

(S)-5-Chloro-8-(1-methylpyrrolidin-2-yl)-
[1,6]naphthyridine

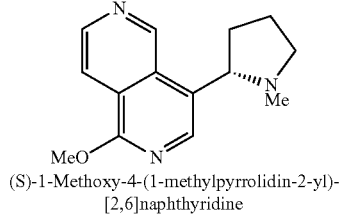

(S)-1-Methoxy-4-(1-methylpyrrolidin-2-yl)-
[2,6]naphthyridine

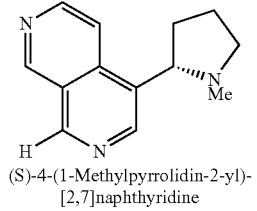

(S)-4-(1-Methylpyrrolidin-2-yl)-
[2,7]naphthyridine

-continued

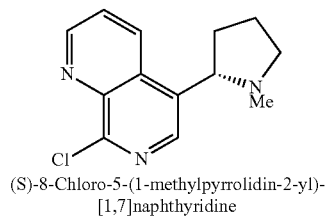

(S)-8-Chloro-5-(1-methylpyrrolidin-2-yl)-
[1,7]naphthyridine

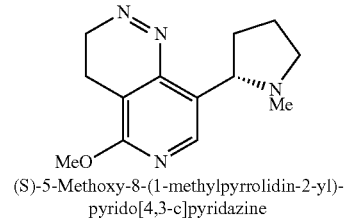

(S)-5-Methoxy-8-(1-methylpyrrolidin-2-yl)-
pyrido[4,3-c]pyridazine

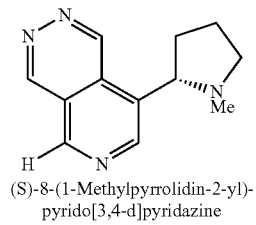

(S)-8-(1-Methylpyrrolidin-2-yl)-
pyrido[3,4-d]pyridazine

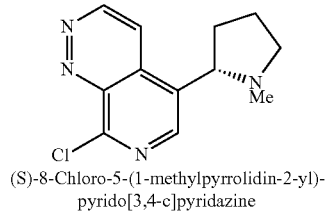

(S)-8-Chloro-5-(1-methylpyrrolidin-2-yl)-
pyrido[3,4-c]pyridazine

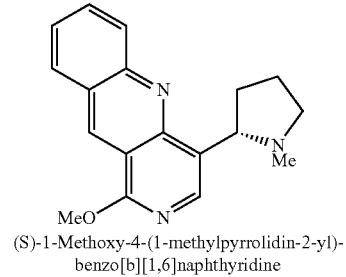

(S)-1-Methoxy-4-(1-methylpyrrolidin-2-yl)-
benzo[b][1,6]naphthyridine

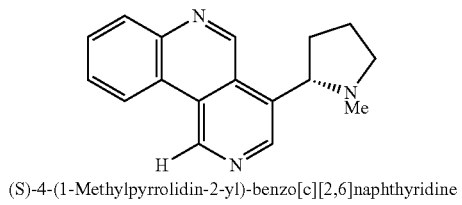

(S)-4-(1-Methylpyrrolidin-2-yl)-benzo[c][2,6]naphthyridine

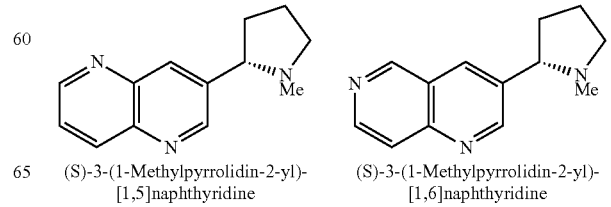

(S)-3-(1-Methylpyrrolidin-2-yl)-      (S)-3-(1-Methylpyrrolidin-2-yl)-
[1,5]naphthyridine                    [1,6]naphthyridine

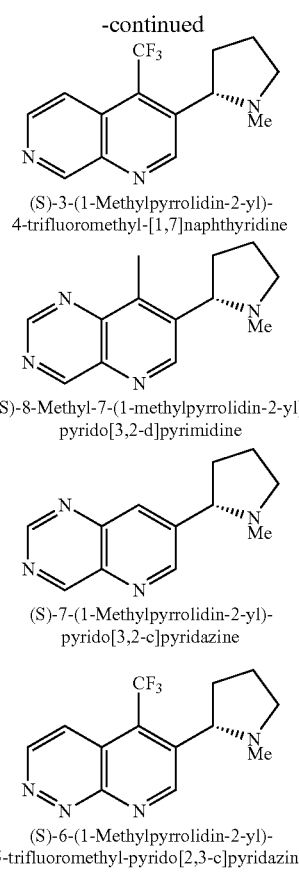

(S)-3-(1-Methylpyrrolidin-2-yl)-
4-trifluoromethyl-[1,7]naphthyridine (S)-8-Methyl-7-(1-methylpyrrolidin-2-yl)-
pyrido[3,2-d]pyrimidine (S)-7-(1-Methylpyrrolidin-2-yl)-
pyrido[3,2-c]pyridazine (S)-6-(1-Methylpyrrolidin-2-yl)-
5-trifluoromethyl-pyrido[2,3-c]pyridazine or a pharmaceutically acceptable salt thereof.

18. The compound of claim 10, wherein at least one X is O; and
   wherein each R' is independently selected from the group consisting of H, alkyl, and halo; or
   wherein an adjacent pair of R's form an additional fused ring as defined in claim 5.

19. The compound of claim 5, wherein said fused ring is a group:

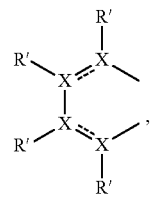

wherein each X and R' are as defined in claim 5.

20. The compound of claim 19, wherein at least one X is independently selected from the group consisting of N and O; and
   wherein each R' is independently selected from the group consisting of H, alkyl, and halo; or
   wherein an adjacent pair of R's together form an additional fused ring as defined in claim 5.

21. The compound of claim 19, wherein at least one X is O; and
   wherein each R' is independently selected from the group consisting of H, alkyl, and halo; or
   wherein an adjacent pair of R's form an additional fused ring as defined in claim 5.

* * * * *

UNITED STATES PATENT AND TRADEMARK OFFICE
CERTIFICATE OF CORRECTION

PATENT NO.       : 8,389,732 B2                                    Page 1 of 3
APPLICATION NO.  : 12/879109
DATED            : March 5, 2013
INVENTOR(S)      : Comins et al.

It is certified that error appears in the above-identified patent and that said Letters Patent is hereby corrected as shown below:

In the Specification:
Column 6, Lines 3-12, (VI): Please correct the compound below:

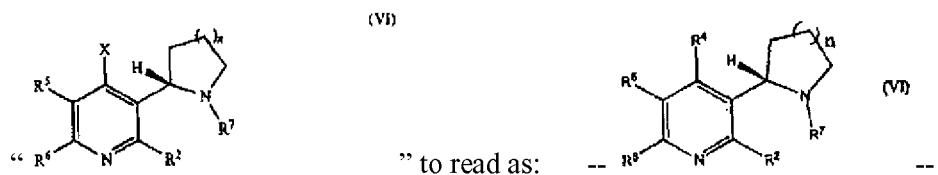

Column 36, Lines 37-44, (X): Please correct the figure below:

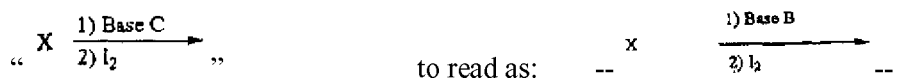

Column 41, Line 55: Please correct "morpholine (125 pt, 1.4 mmol, 1.2 eq),"
to read -- morpholine (125 µl, 1.4 mmol, 1.2 eq), --

In the Claims:
Column 43, Claim 1, Lines 57-67: Please correct the compound below:

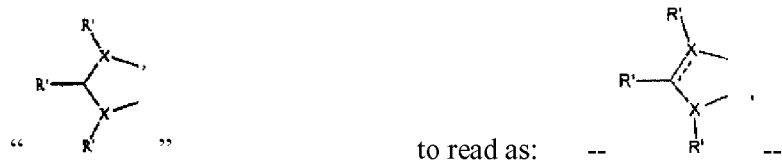

Signed and Sealed this
Nineteenth Day of August, 2014

Michelle K. Lee
*Deputy Director of the United States Patent and Trademark Office*

CERTIFICATE OF CORRECTION (continued)
U.S. Pat. No. 8,389,732 B2

Column 44, Claim 1, Lines 21-29: Please correct the compound below:

Column 44, Claim 1, Lines 48-58: Please correct the compound below:

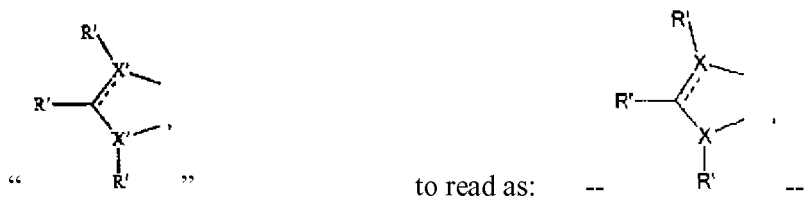

Column 46, Claim 5, Lines 12-18: Please correct the compound below:

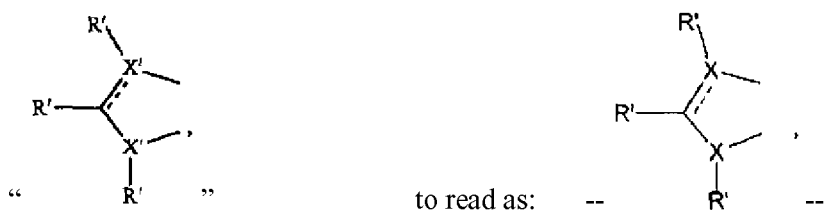

Column 46, Claim 5, Line 42: Please correct "pair of R's to together"
to read -- pair of R's together --

Column 52, Claim 14, Lines 31-39: Please correct the compound below:

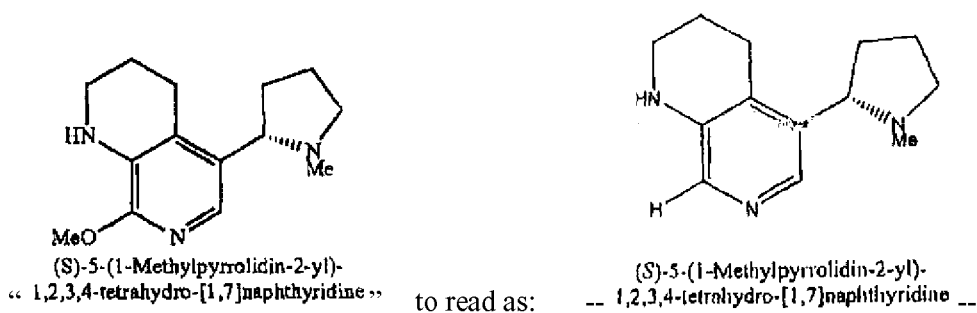

CERTIFICATE OF CORRECTION (continued)
U.S. Pat. No. 8,389,732 B2

Column 52, Claim 15, Lines 47-56: Please correct the compound below:

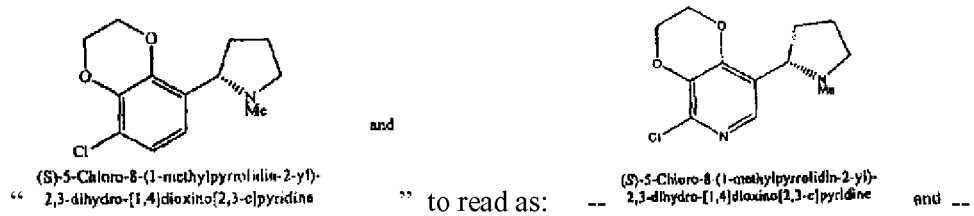

Column 54, Claim 17, Lines 10-20: Please correct the compound below:

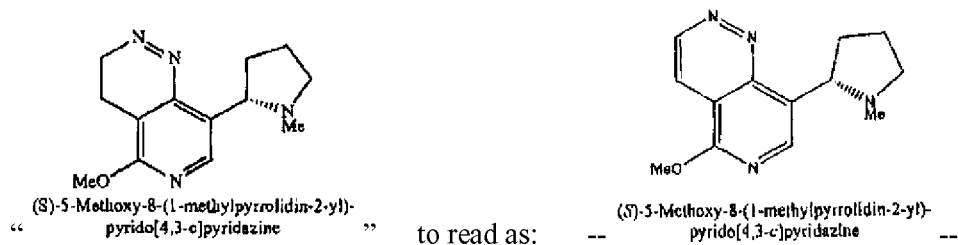

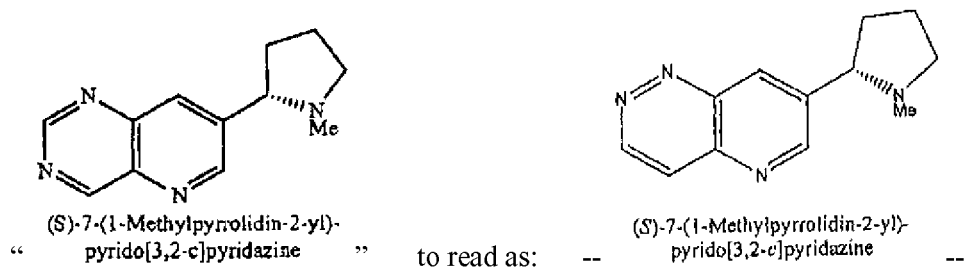

Column 55, Claim 17, Lines 18-24: Please correct the compound below: